US011078254B2

(12) United States Patent
Tateno et al.

(10) Patent No.: US 11,078,254 B2
(45) Date of Patent: Aug. 3, 2021

(54) METHOD FOR IMMOBILIZING LECTIN

(71) Applicants: National Institute of Advanced Industrial Science and Technology, Tokyo (JP); Nissan Chemical Corporation, Tokyo (JP); National University Corporation Kyoto Institute of Technology, Kyoto (JP)

(72) Inventors: Hiroaki Tateno, Ibaraki (JP); Junko Katayama, Tokyo (JP); Kazutaka Matoba, Chiba (JP); Yoichi Kumada, Kyoto (JP)

(73) Assignees: National Institute of Advanced Industrial Science and Technology, Tokyo (JP); Nissan Chemical Corporation, Tokyo (JP); National University Corporation Kyoto Institute of Technology, Tokyo (JP)

( * ) Notice: Subject to any disclaimer, the term of this patent is extended or adjusted under 35 U.S.C. 154(b) by 0 days.

(21) Appl. No.: 16/604,565

(22) PCT Filed: Apr. 11, 2018

(86) PCT No.: PCT/JP2018/015163
§ 371 (c)(1),
(2) Date: Oct. 10, 2019

(87) PCT Pub. No.: WO2018/190357
PCT Pub. Date: Oct. 18, 2018

(65) Prior Publication Data
US 2020/0123222 A1 Apr. 23, 2020

(30) Foreign Application Priority Data
Apr. 11, 2017 (JP) .............................. JP2017-078414

(51) Int. Cl.
*C07K 7/06* (2006.01)
*C07K 14/195* (2006.01)
*C07K 17/08* (2006.01)
*C07K 17/14* (2006.01)
*C07K 19/00* (2006.01)
*G01N 33/545* (2006.01)
*G01N 33/551* (2006.01)
*G01N 33/566* (2006.01)
*C07K 14/705* (2006.01)
*C07K 17/00* (2006.01)
*C12N 15/62* (2006.01)
*G01N 33/543* (2006.01)

(52) U.S. Cl.
CPC ............ *C07K 14/7056* (2013.01); *C07K 7/06* (2013.01); *C07K 14/195* (2013.01); *C07K 17/00* (2013.01); *C07K 17/08* (2013.01); *C07K 17/14* (2013.01); *C12N 15/62* (2013.01); *G01N 33/543* (2013.01); *G01N 33/545* (2013.01); *G01N 33/54353* (2013.01); *G01N 33/551* (2013.01); *G01N 33/566* (2013.01); *C07K 2319/00* (2013.01); *C07K 2319/20* (2013.01); *C07K 2319/40* (2013.01)

(58) Field of Classification Search
CPC .... C07K 7/06; C07K 14/195; C07K 14/7056; C07K 17/00; C07K 17/02; C07K 17/06; C07K 17/08; C07K 17/14; C07K 2319/00; C07K 2319/20; G01N 33/543; G01N 33/54353; G01N 33/545; G01N 33/551; G01N 33/566; G01N 33/68
See application file for complete search history.

(56) References Cited

U.S. PATENT DOCUMENTS

| | | | |
|---|---|---|---|
| 9,850,316 B2 * | 12/2017 | Kumada | C07K 16/065 |
| 2007/0160533 A1 * | 7/2007 | Chen | A61P 17/00 424/1.69 |
| 2011/0045538 A1 | 2/2011 | Kumada et al. | |
| 2011/0301057 A1 * | 12/2011 | Propheter | C07K 1/1077 506/9 |
| 2015/0018534 A1 | 1/2015 | Kumada et al. | |
| 2015/0038675 A1 | 2/2015 | Kumada et al. | |

(Continued)

FOREIGN PATENT DOCUMENTS

| | | |
|---|---|---|
| JP | 2011-168505 A | 9/2011 |
| JP | 5553336 B2 | 7/2014 |

(Continued)

OTHER PUBLICATIONS

Kumada, Y., et al. "Improved lectin ELISA for glycosylation analysis of biomarkers using PS-tag-fused single-chain Fv", Journal of Immunological Methods, vol. 384, pp. 15-22 (2012).

(Continued)

*Primary Examiner* — Jeffrey E. Russel
(74) *Attorney, Agent, or Firm* — Mintz Levin Cohn Ferris Glovsky and Popeo, P.C.; Peter F. Corless; Joohee Lee

(57) ABSTRACT

Provided is a highly sensitive and less expensive lectin-immobilized base material (for example, a lectin plate), such as lectin-immobilized base material having stable qualities and being able to be sufficiently washed after a target sugar chain-containing antigen binds thereto. Further provided is a method for immobilizing lectin to a base material therefor. Particularly provided are: a method whereby a lectin-peptide fusion, in which a peptide capable of adsorbing to a base material surface such as a polystyrene (PS) tag is fused with the N-terminal side or C-terminal side of lectin capable of recognizing a target sugar chain, is immobilized on the peptide side to a base material; and a lectin-immobilized base material produced by this method. By using the lectin-immobilized base material, a target sugar chain-containing antigen can be highly sensitively and evenly measured and, moreover, target sugar chain-containing cells, etc. can be separated (concentrated and harvested).

18 Claims, 30 Drawing Sheets
Specification includes a Sequence Listing.

(56) References Cited

U.S. PATENT DOCUMENTS

| | | | |
|---|---|---|---|
| 2015/0044692 A1* | 2/2015 | Kleinfeld | G01N 21/6428 |
| | | | 435/7.8 |
| 2015/0111218 A1 | 4/2015 | Tateno et al. | |
| 2015/0204870 A1 | 7/2015 | Tateno et al. | |
| 2018/0022830 A1 | 1/2018 | Kumada et al. | |
| 2018/0038847 A1* | 2/2018 | Tateno | C07H 5/04 |

FOREIGN PATENT DOCUMENTS

| | | |
|---|---|---|
| JP | 5655254 B2 | 1/2015 |
| JP | 5851391 B2 | 2/2016 |
| WO | 2009-101807 A1 | 8/2009 |
| WO | 2013-065302 A1 | 5/2013 |
| WO | 2013-122061 A1 | 8/2013 |
| WO | 2013-128914 A1 | 9/2013 |
| WO | 2016-129695 A1 | 8/2016 |
| WO | WO-2016147514 A1 * | 9/2016 ....... G01N 33/57484 |

OTHER PUBLICATIONS

Kumada, Y., et al., "Screening and Characterization of Affinity Peptide Tags Specific to Polystyrene Supports for the Orientated Immobilization of Proteins", Biotechnol. Prog. vol. 22, pp. 401-405 (2006).

Propheter, D., et al., "Fabrication of an Oriented Lectin Microarray", ChemBioChem., vol. 11, pp. 1203-1207 (2010).

International Search Report dated Jul. 10, 2018 issued in PCT/JP2018/015163.

* cited by examiner

[FIG. 1]
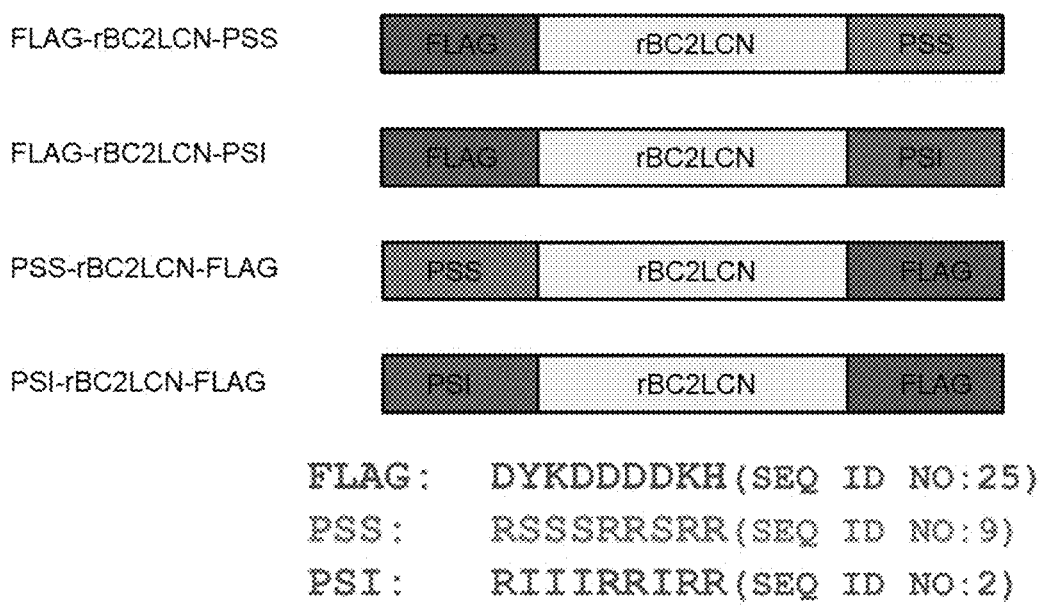

[FIG. 2]
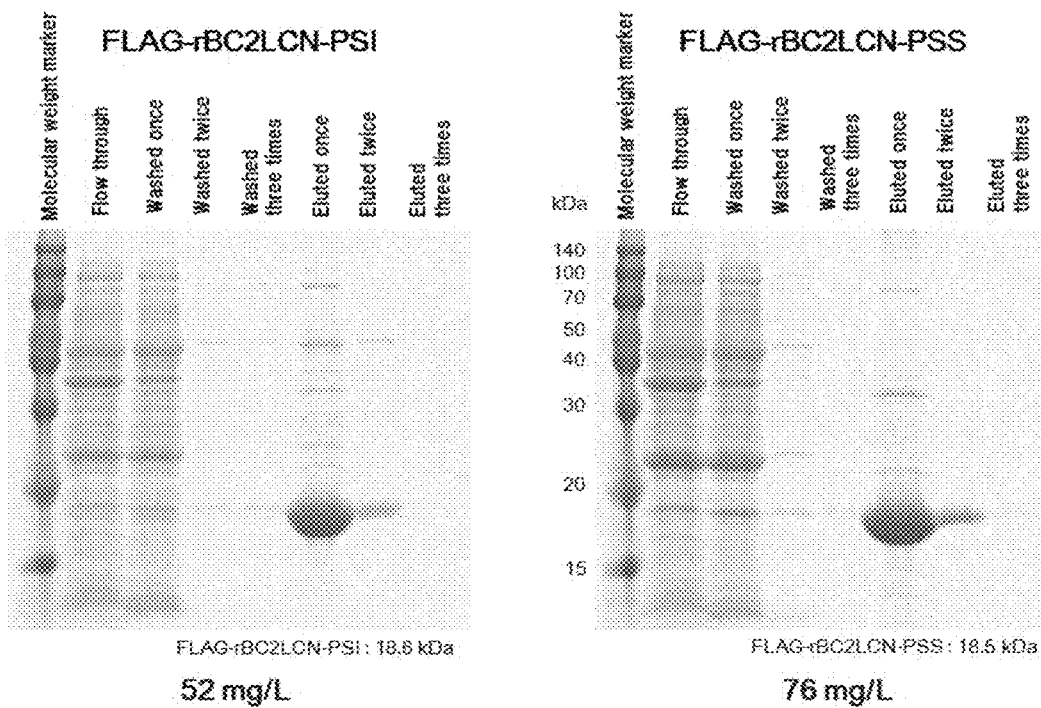

[FIG. 3]
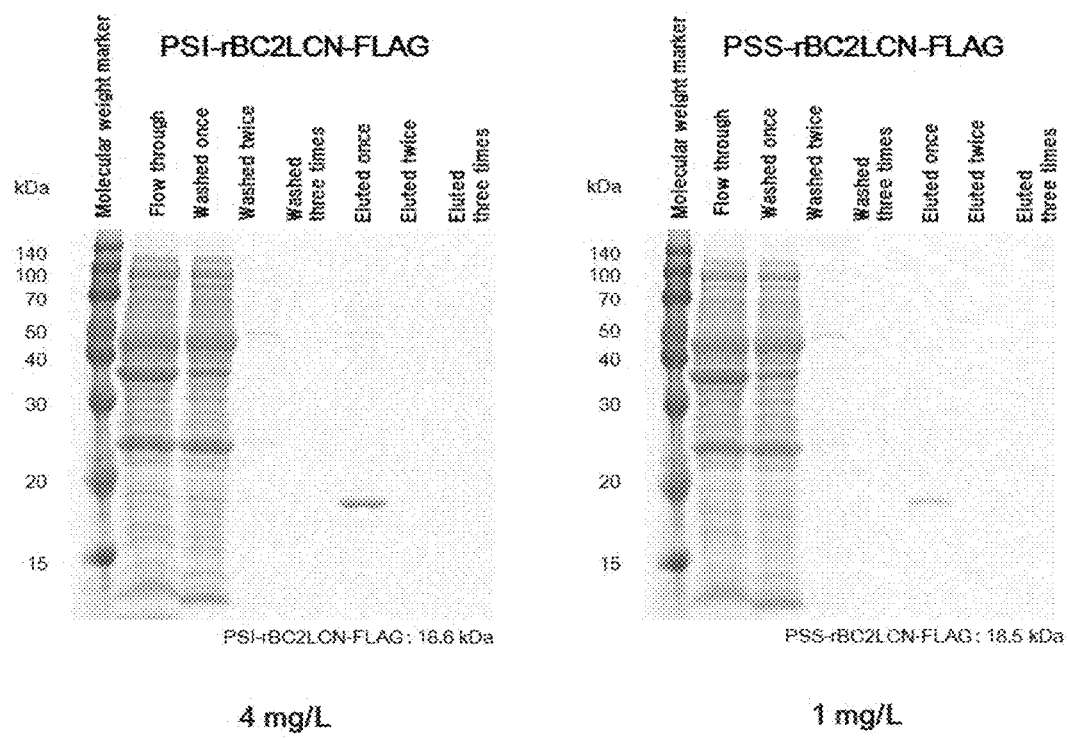

[FIG. 4]
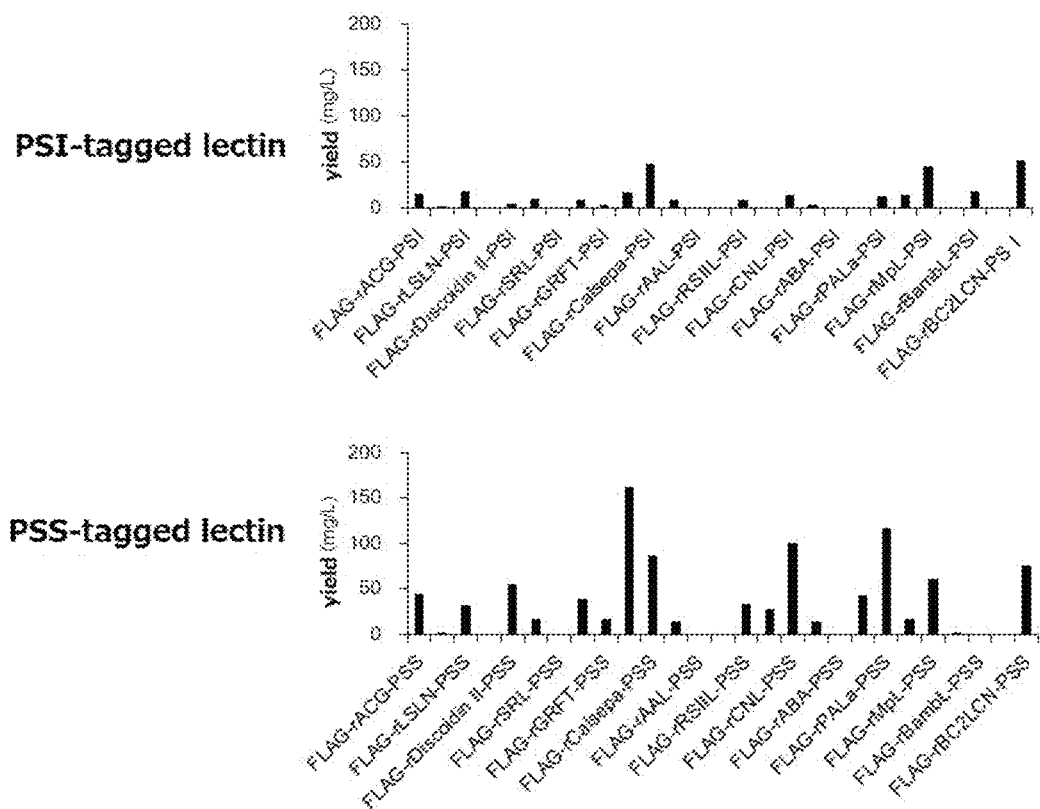

[FIG. 5A]
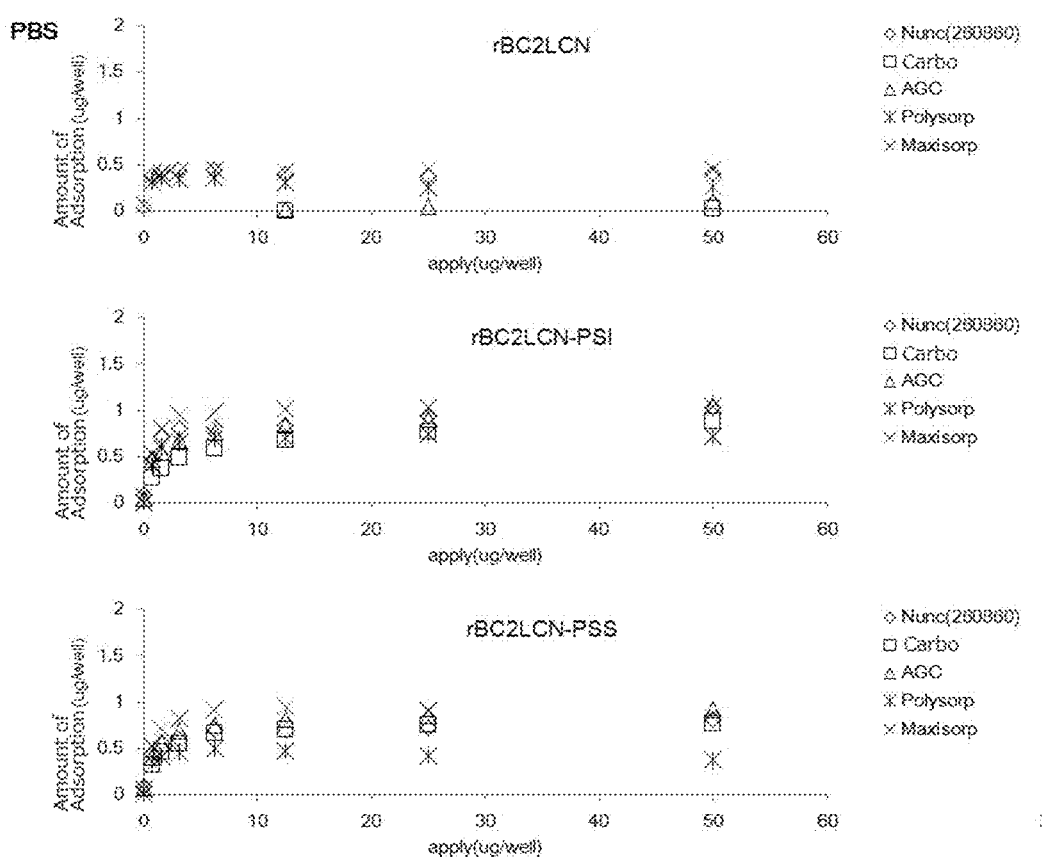

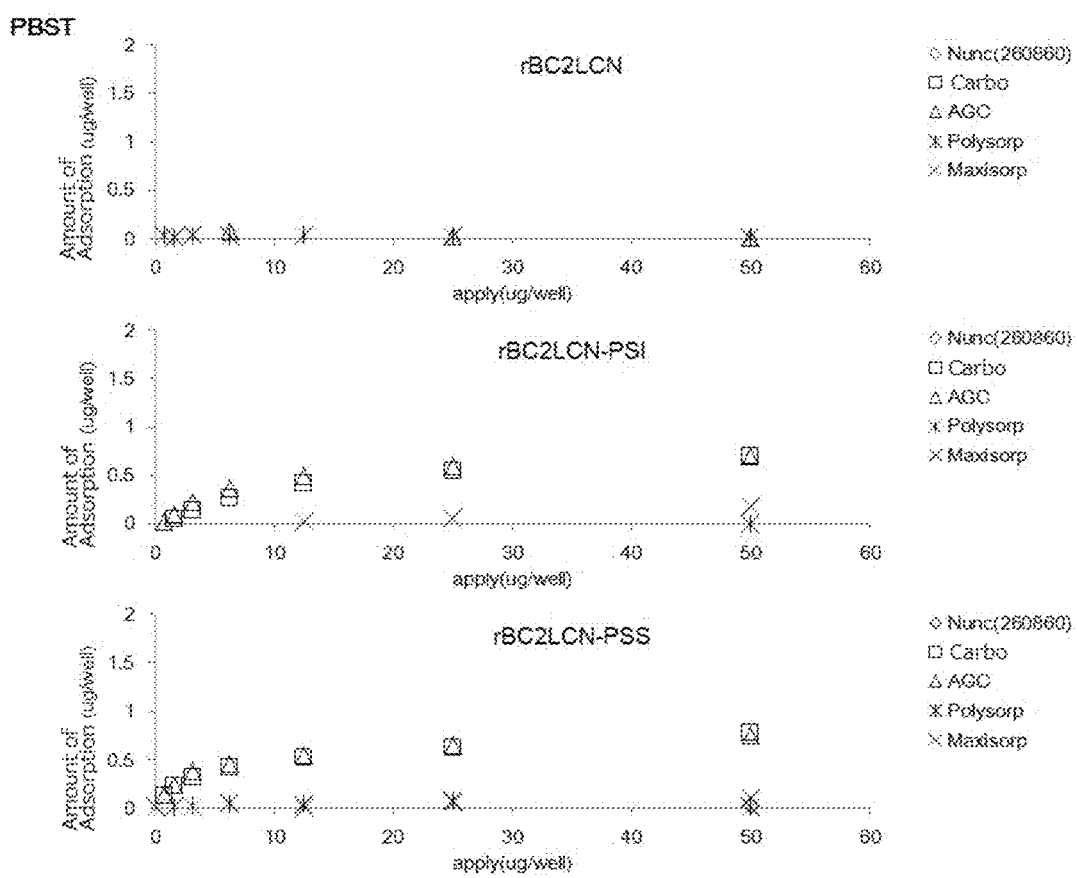
[FIG. 5B]

[FIG. 6]
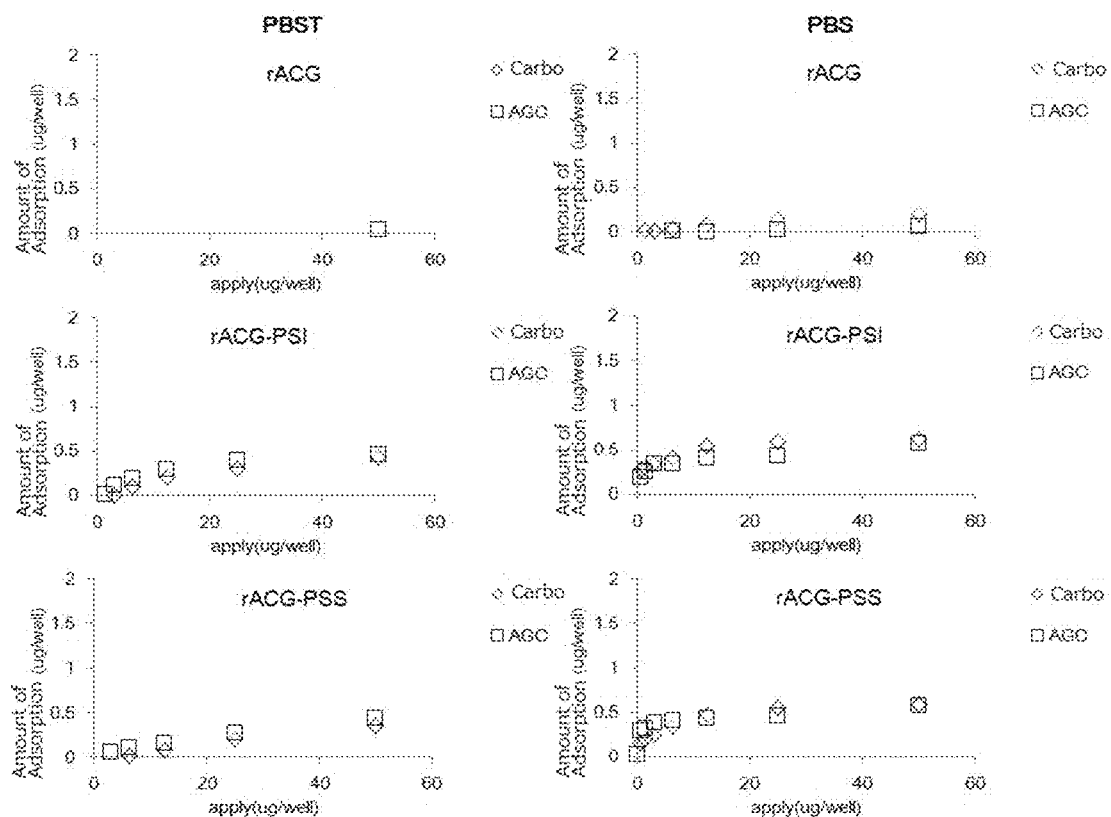

[FIG. 7]
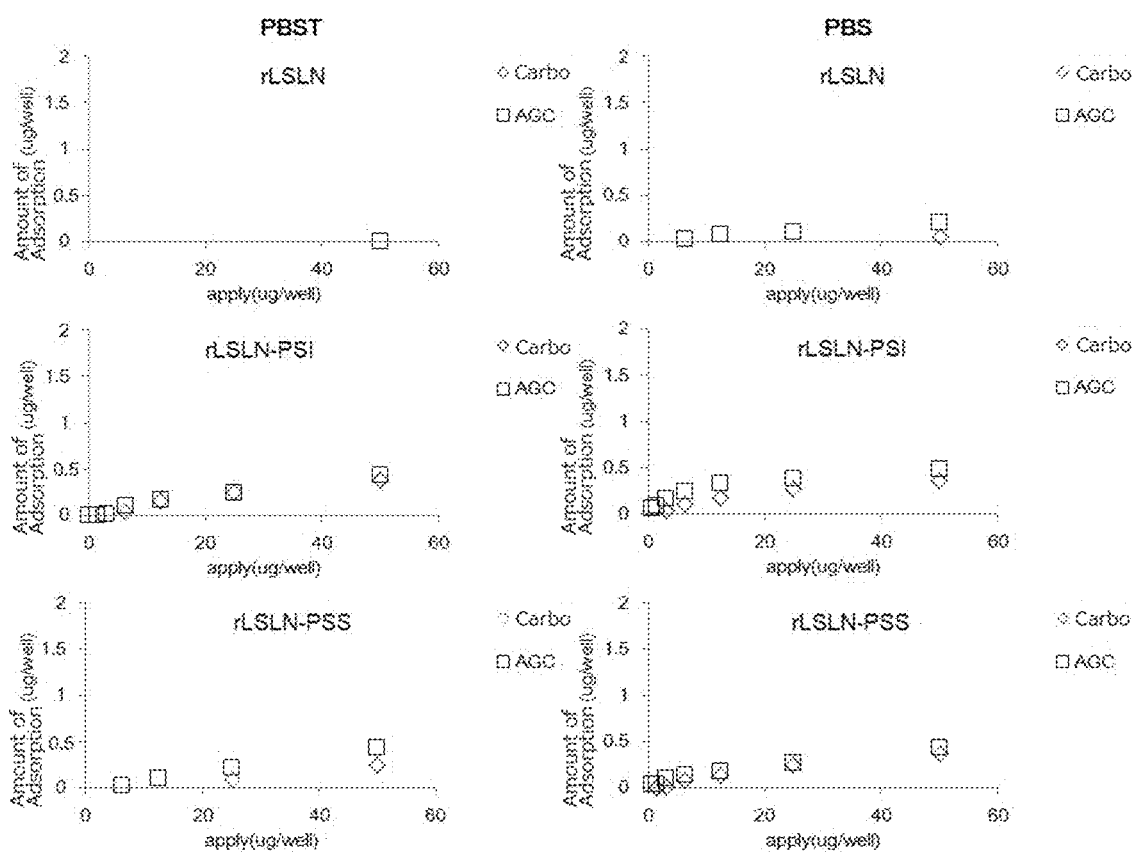

[FIG. 8]
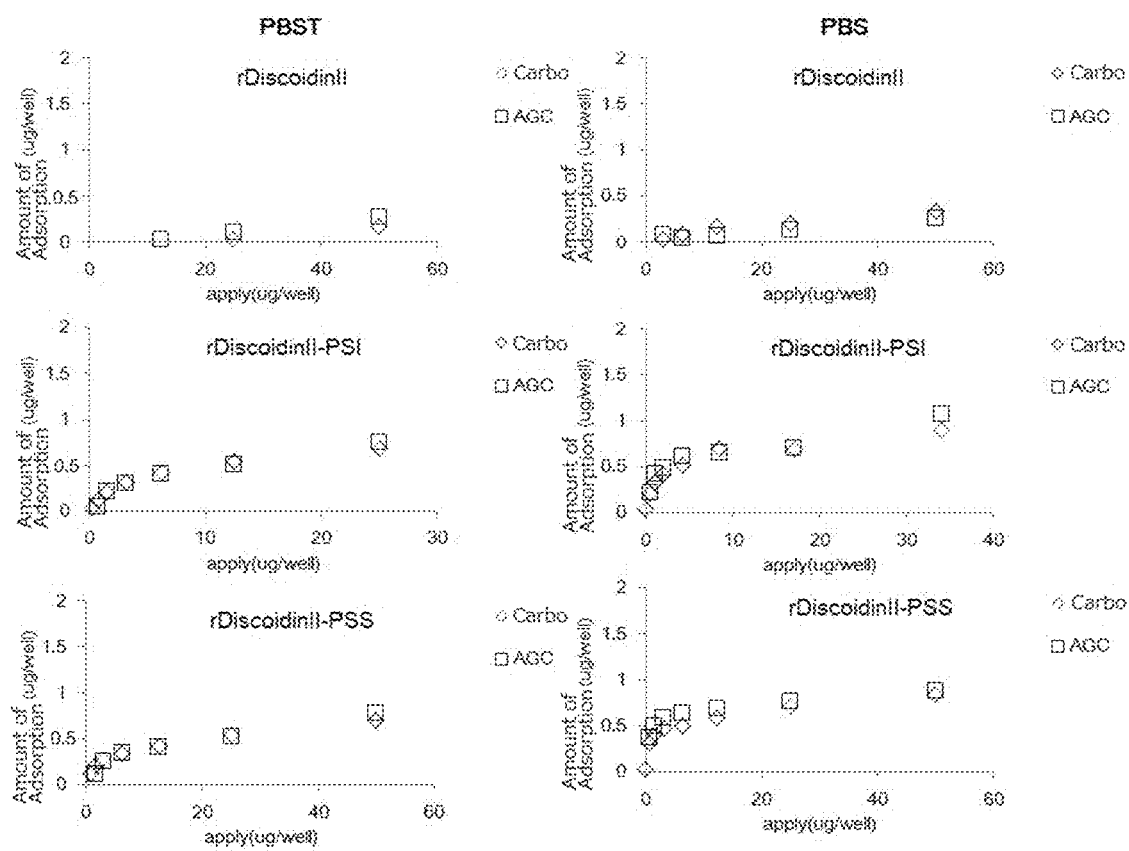

[FIG. 9]
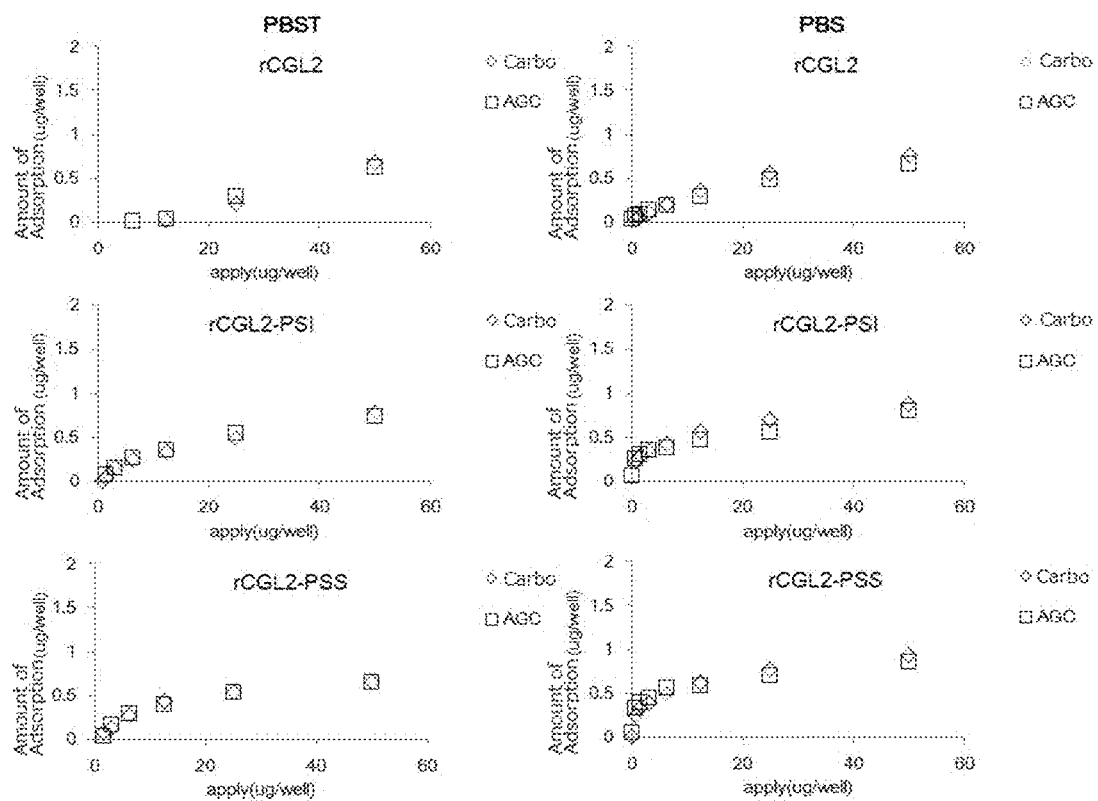

[FIG. 10]
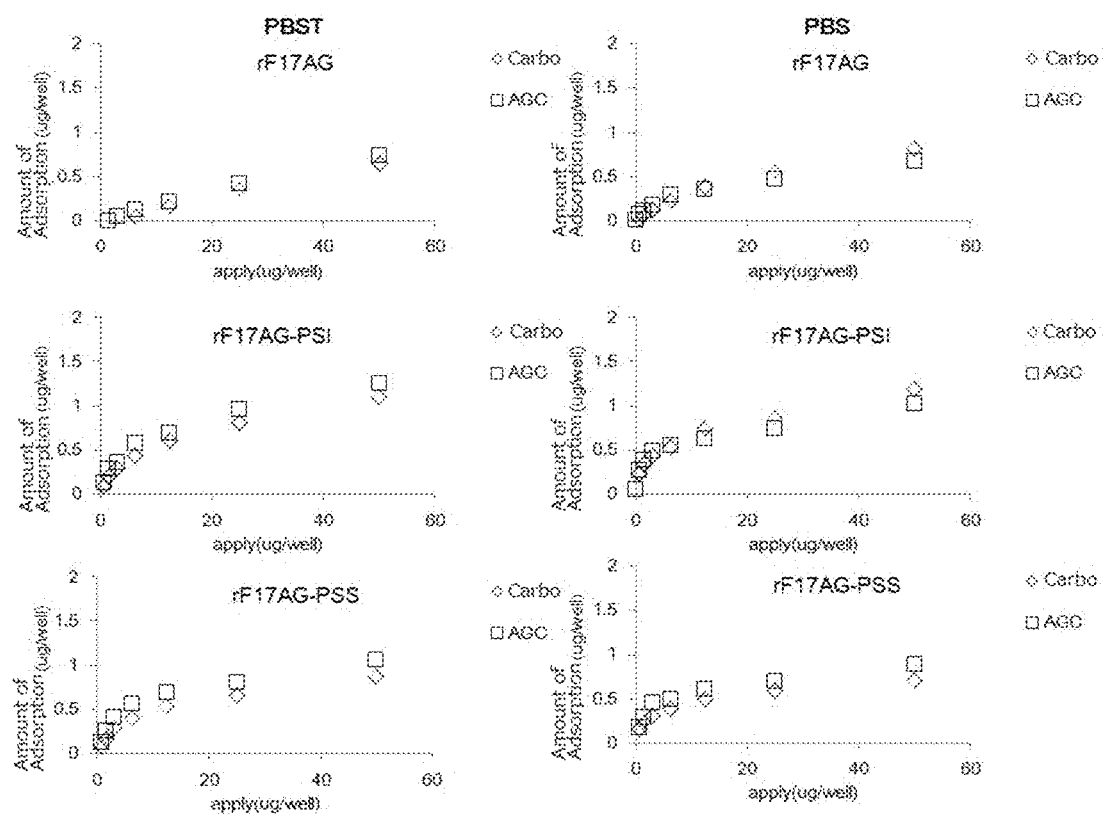

[FIG. 11]
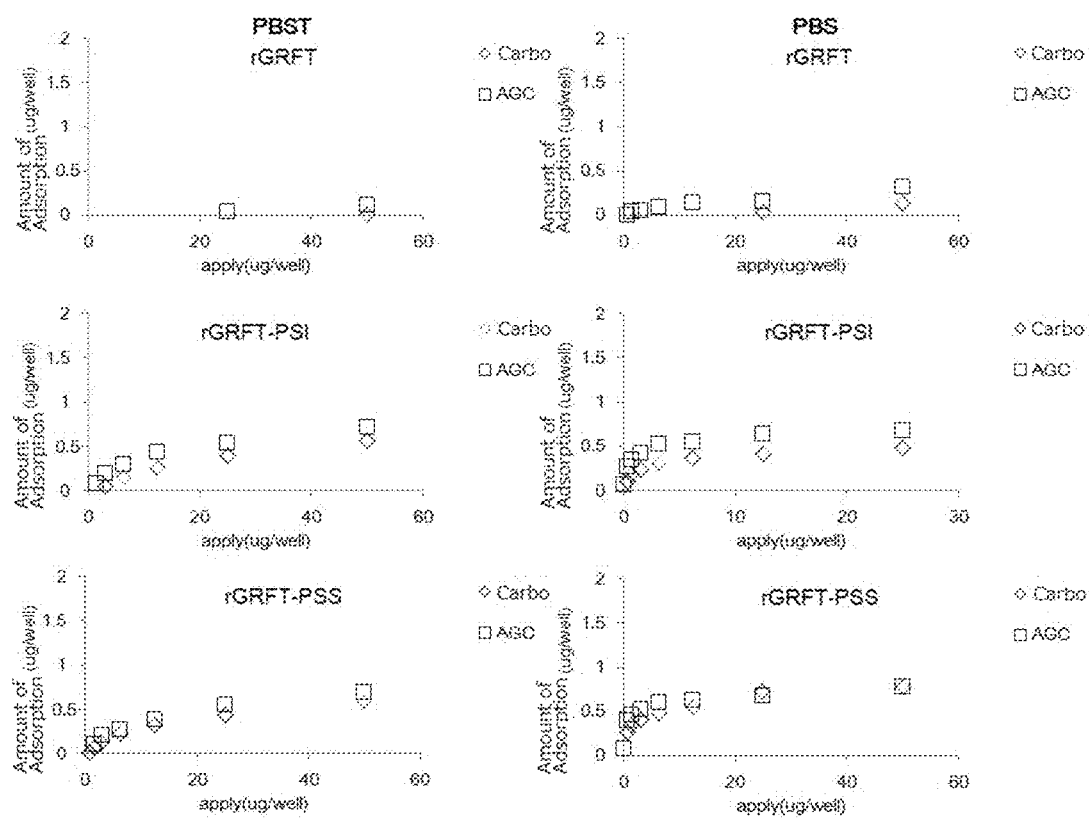

[FIG. 12]
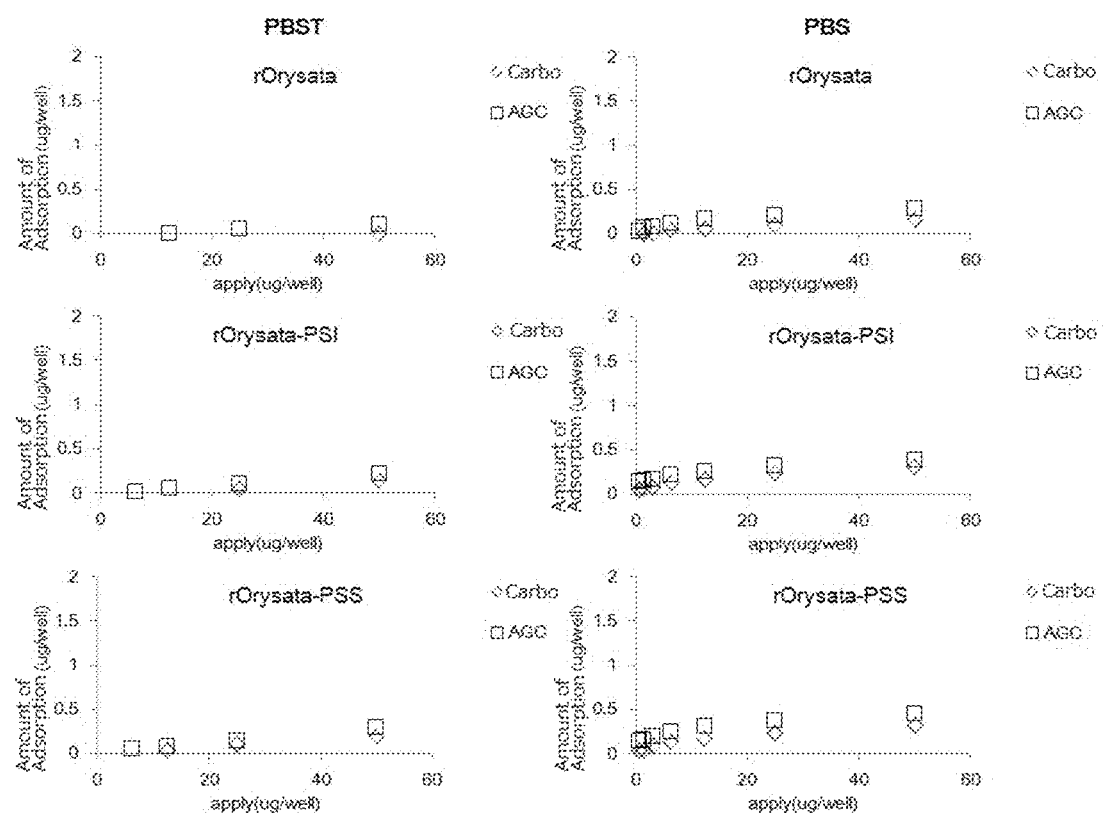

[FIG. 13]
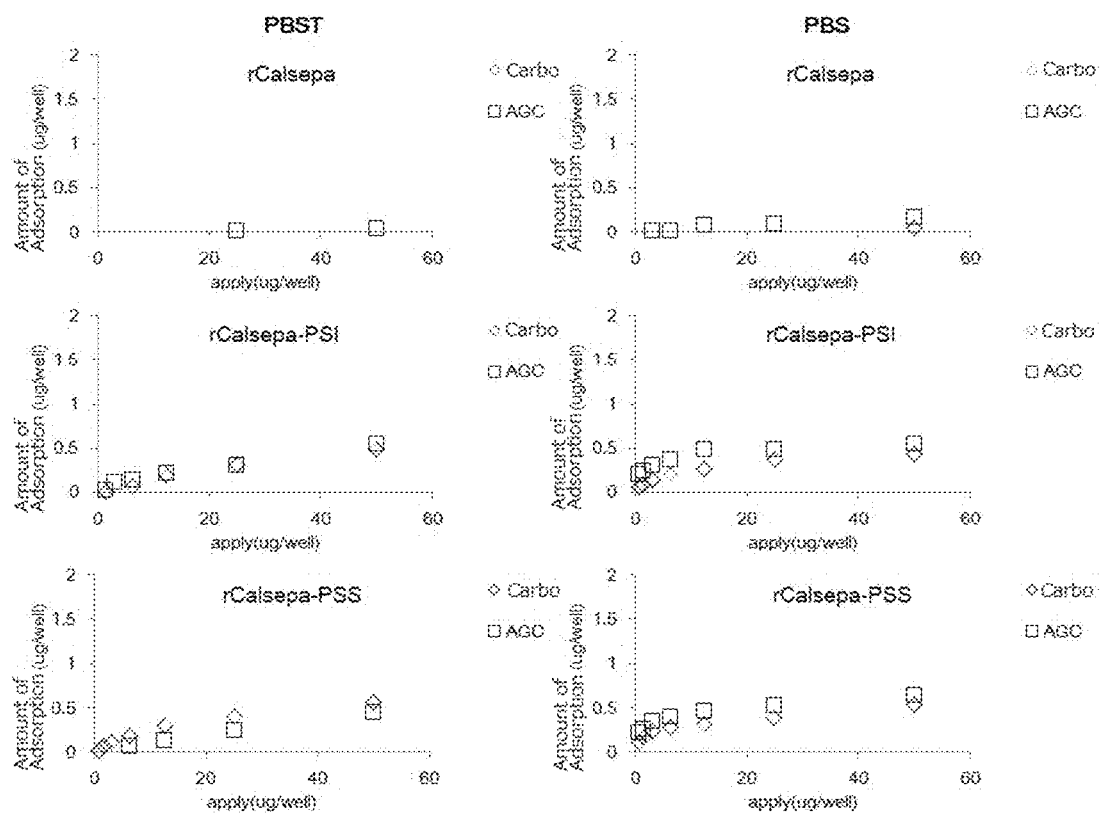

[FIG. 14]
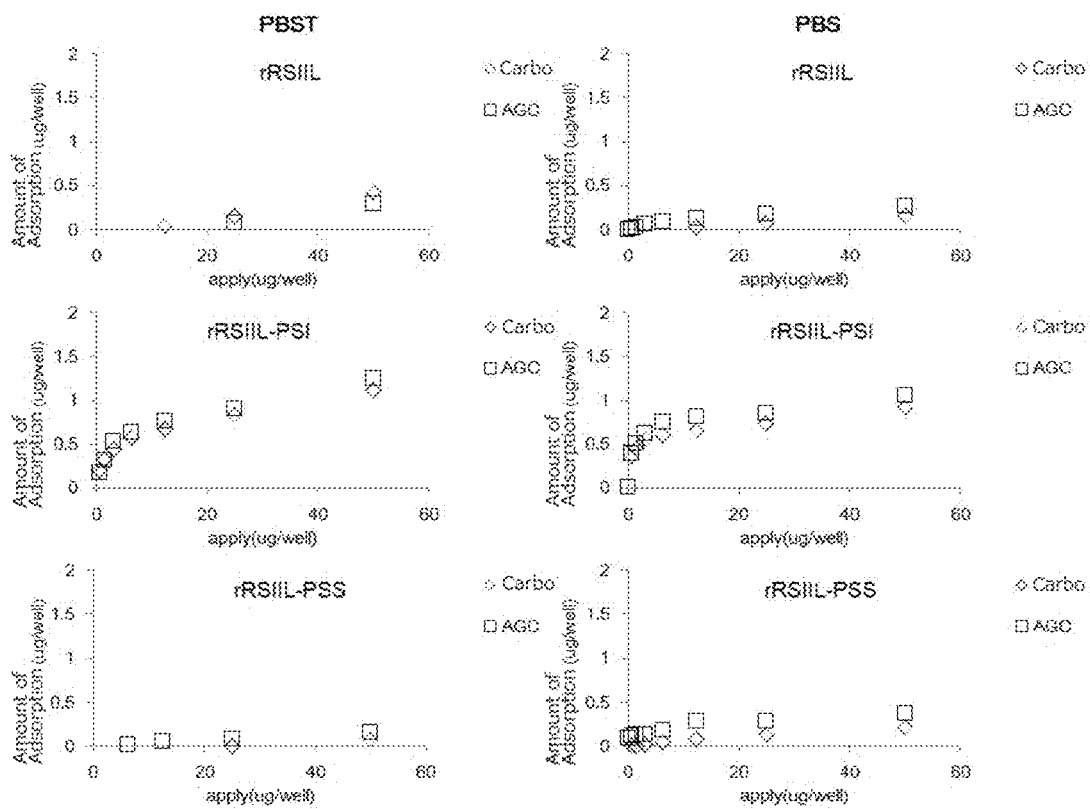

[FIG. 15]
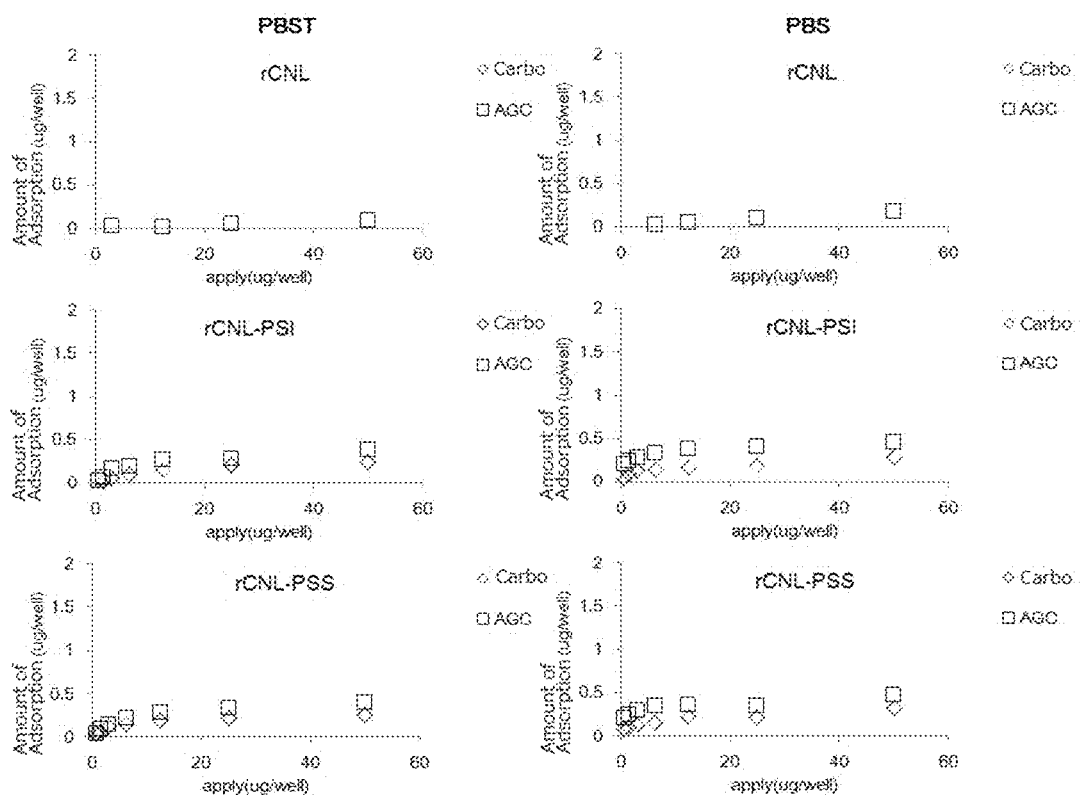

[FIG. 16]
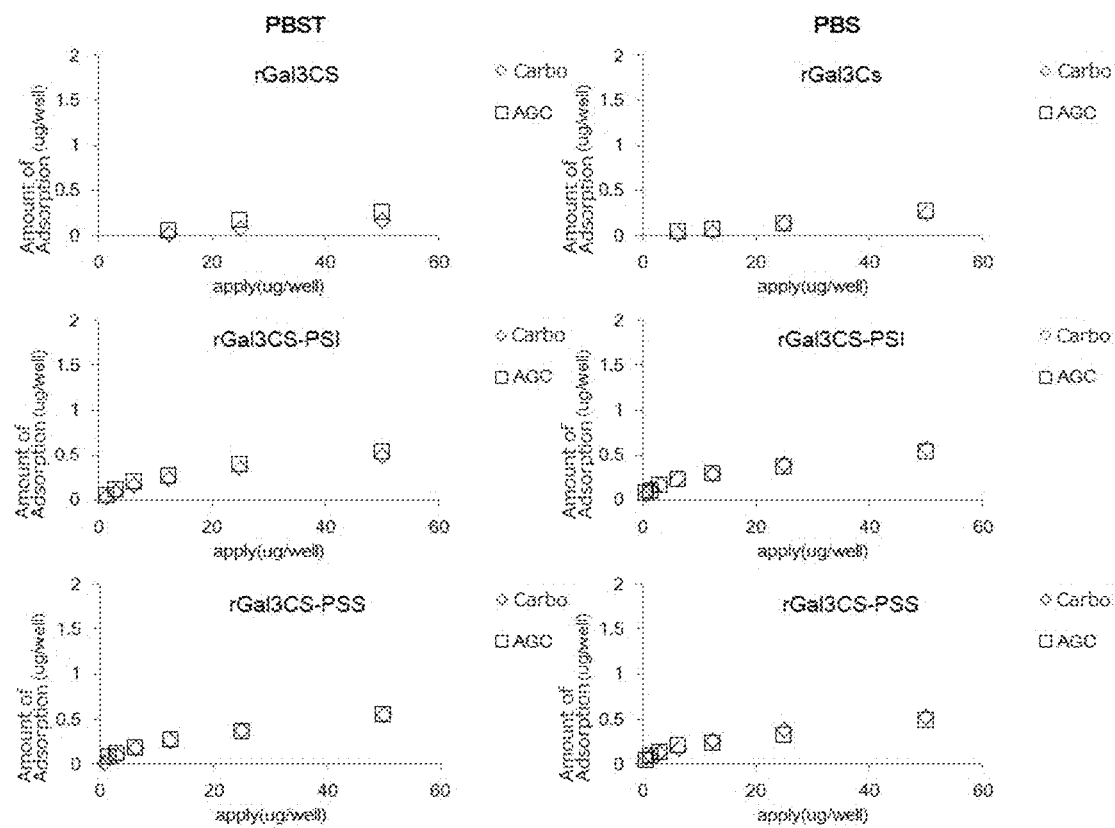

[FIG. 17]
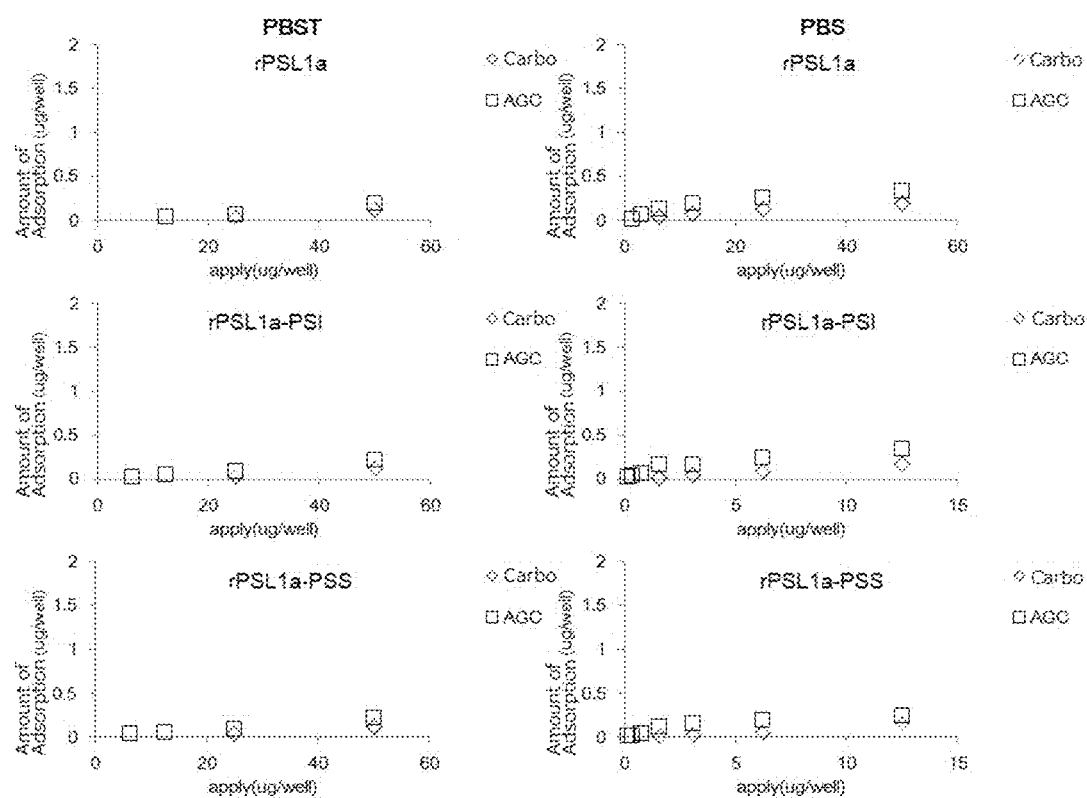

[FIG. 18]
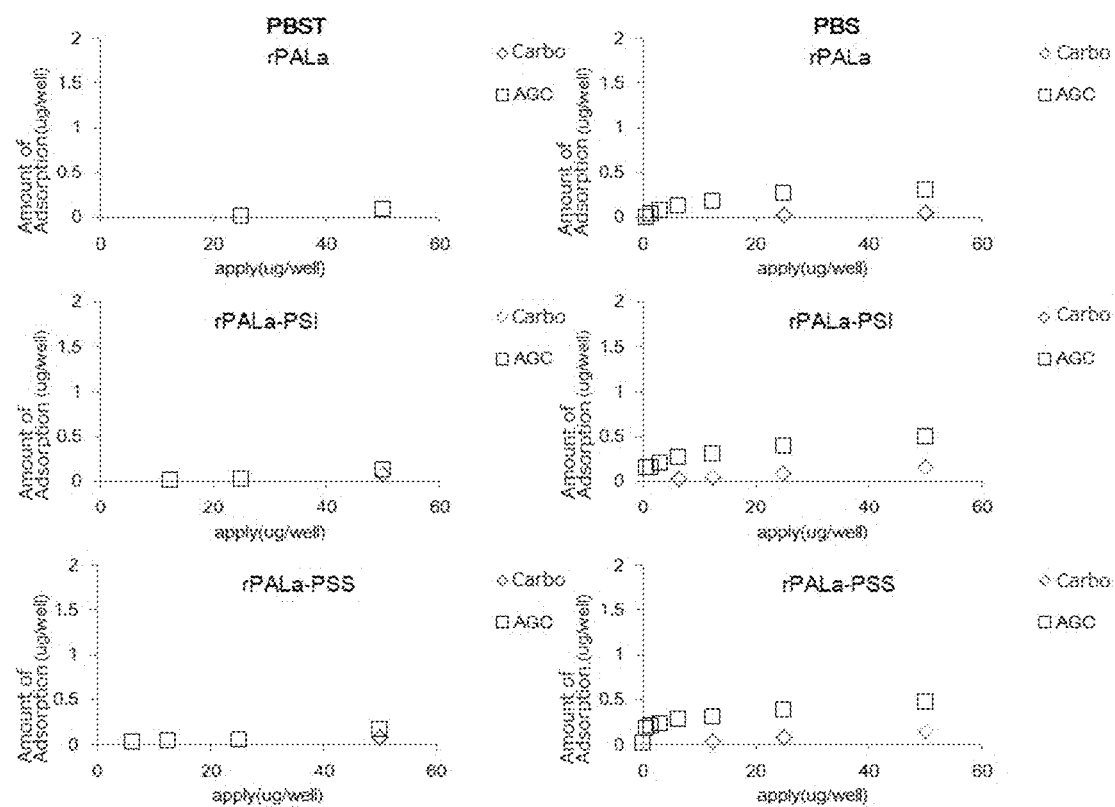

[FIG. 19]
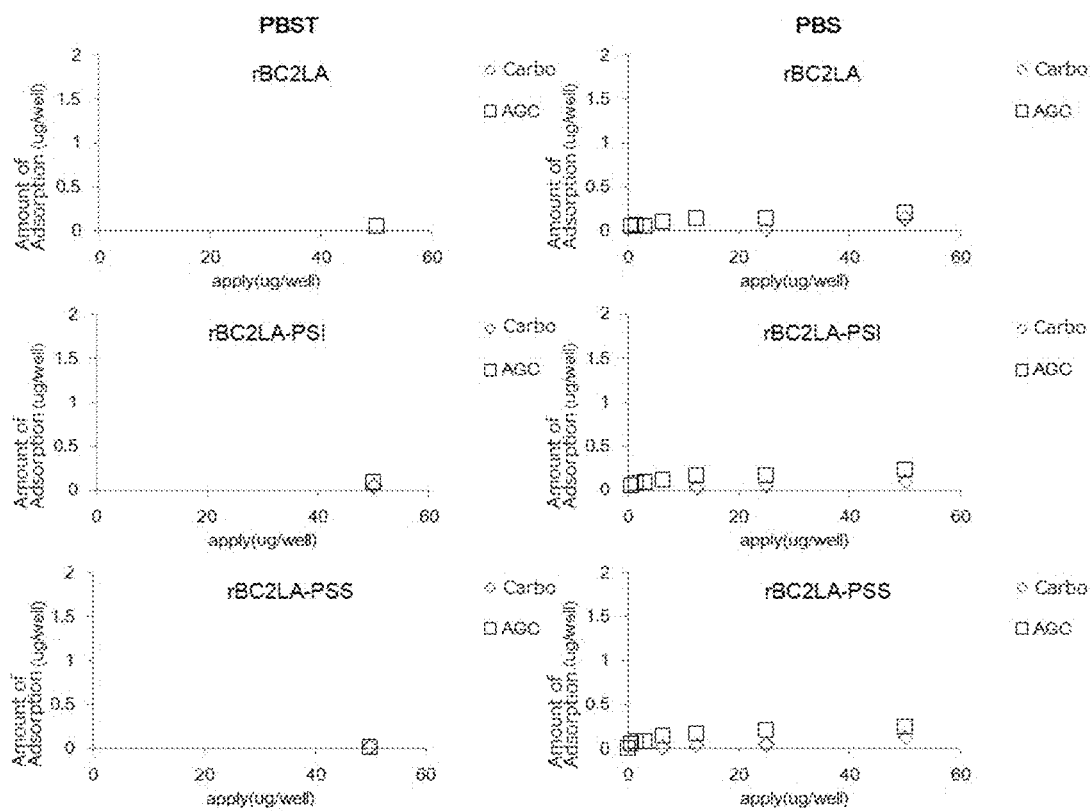

[FIG. 20]
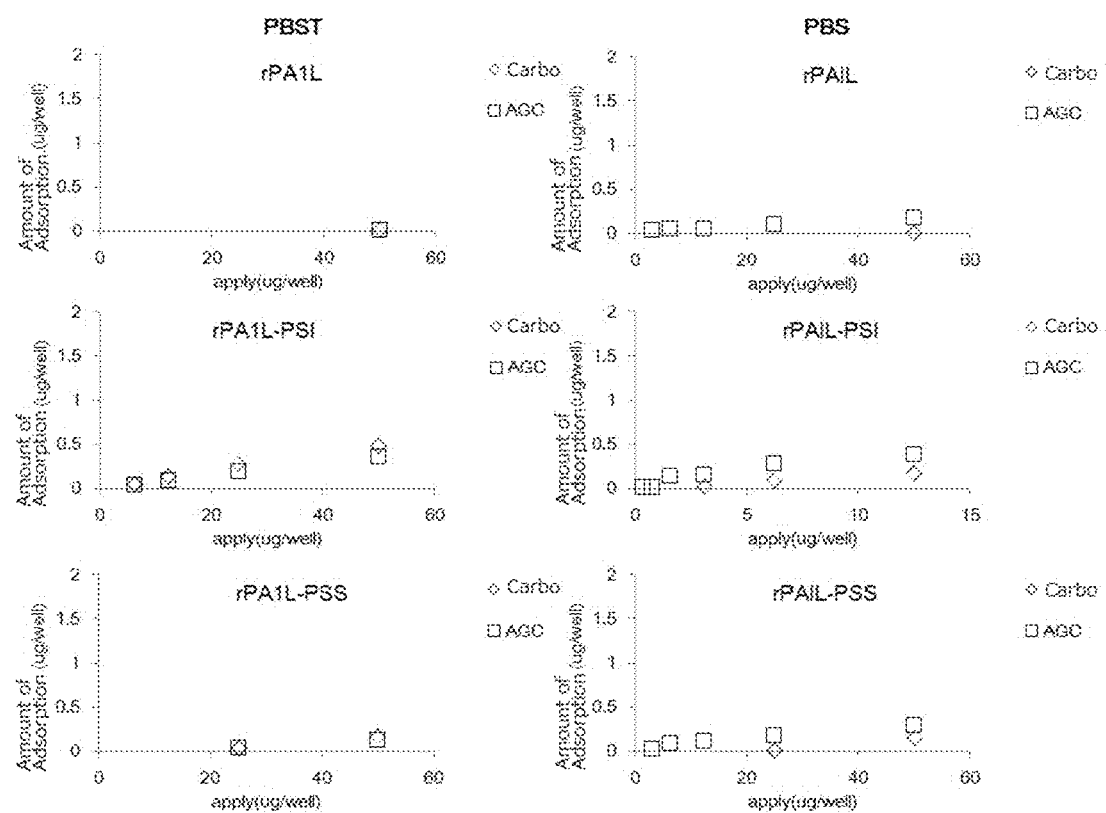

[FIG. 21]
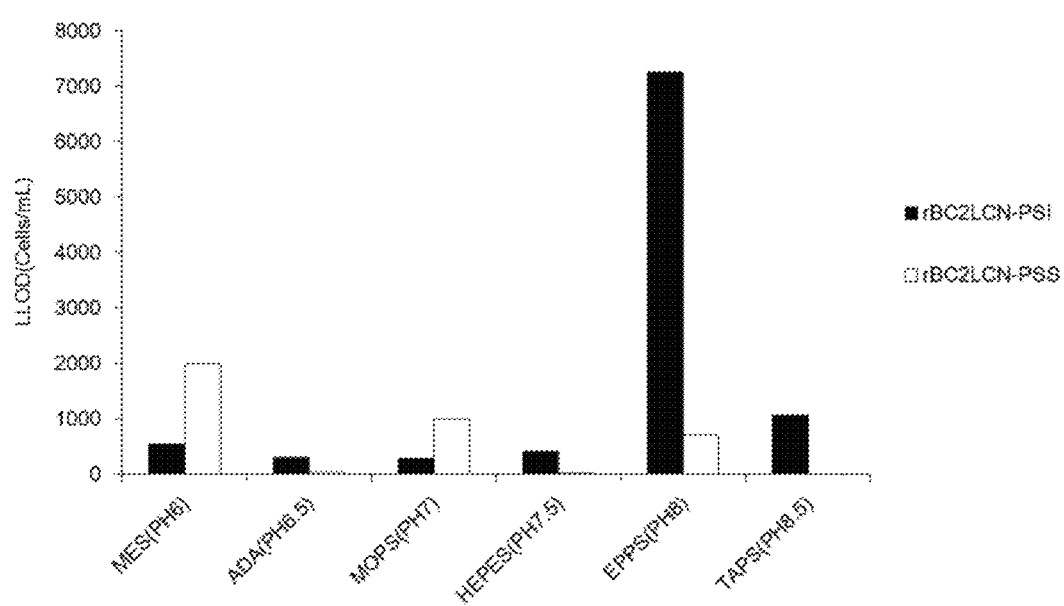

[FIG. 22]
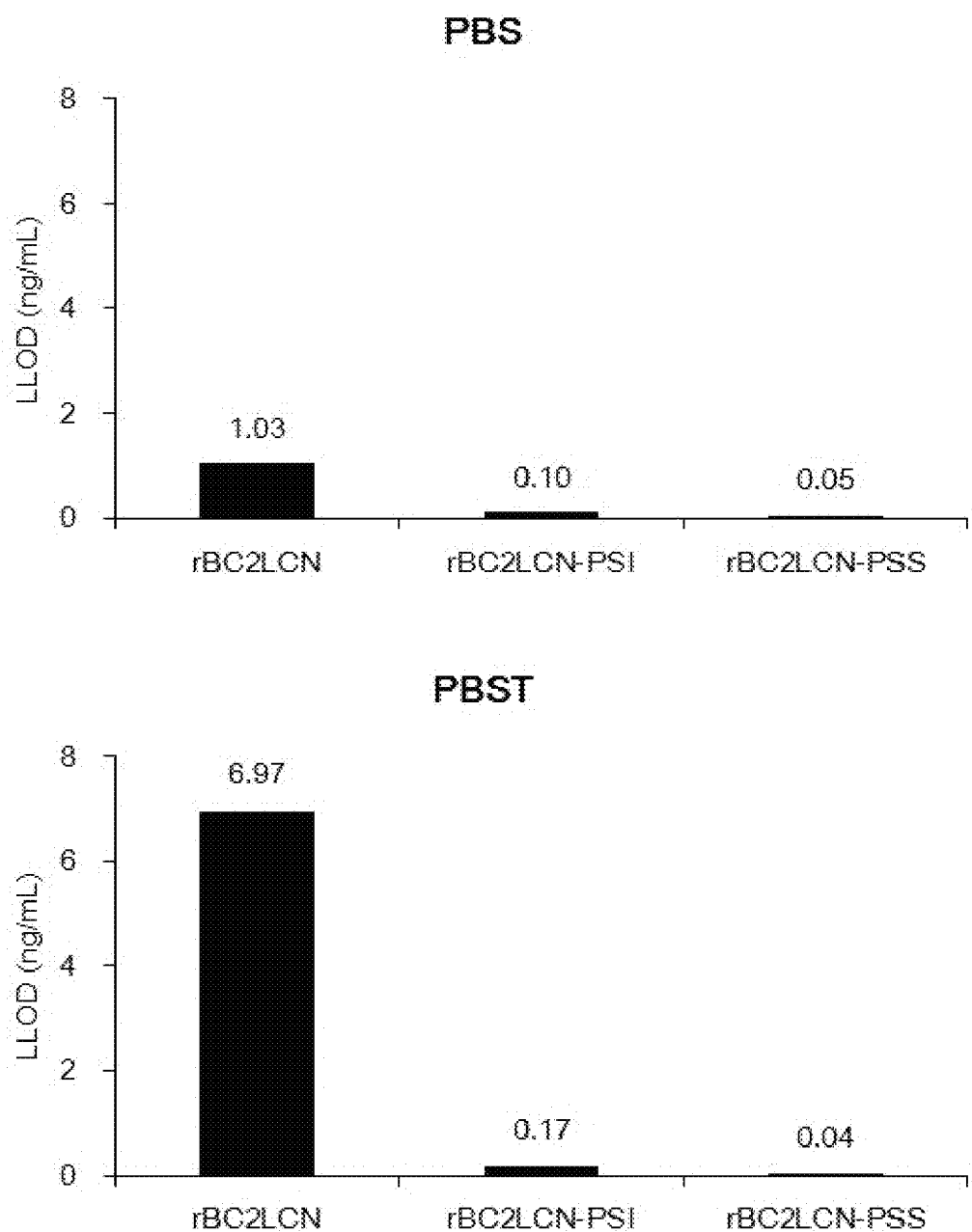

[FIG. 23]
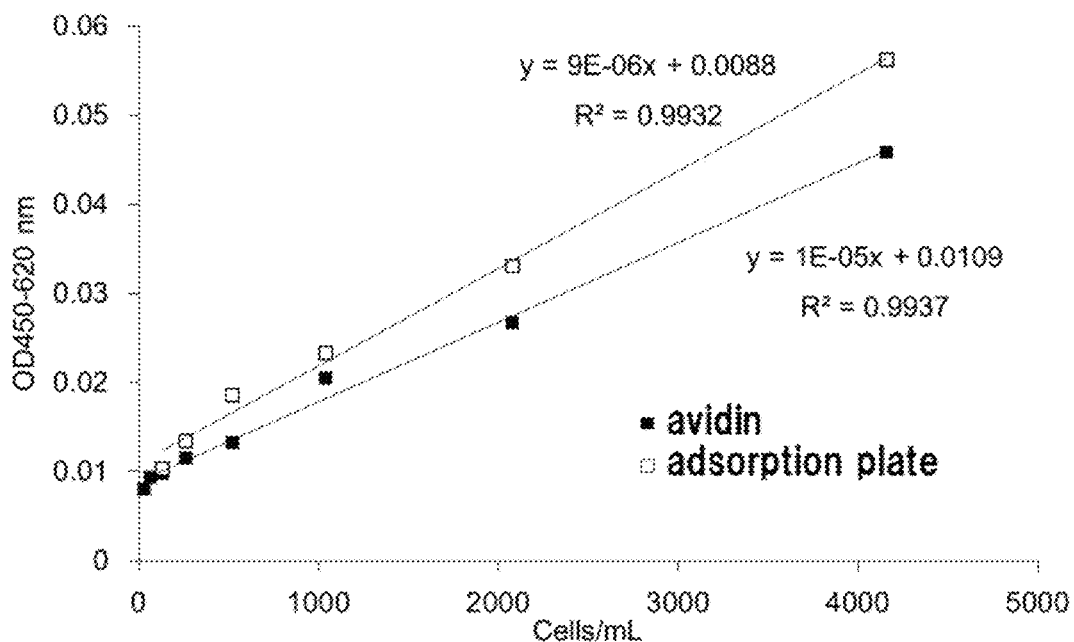
[FIG. 24]
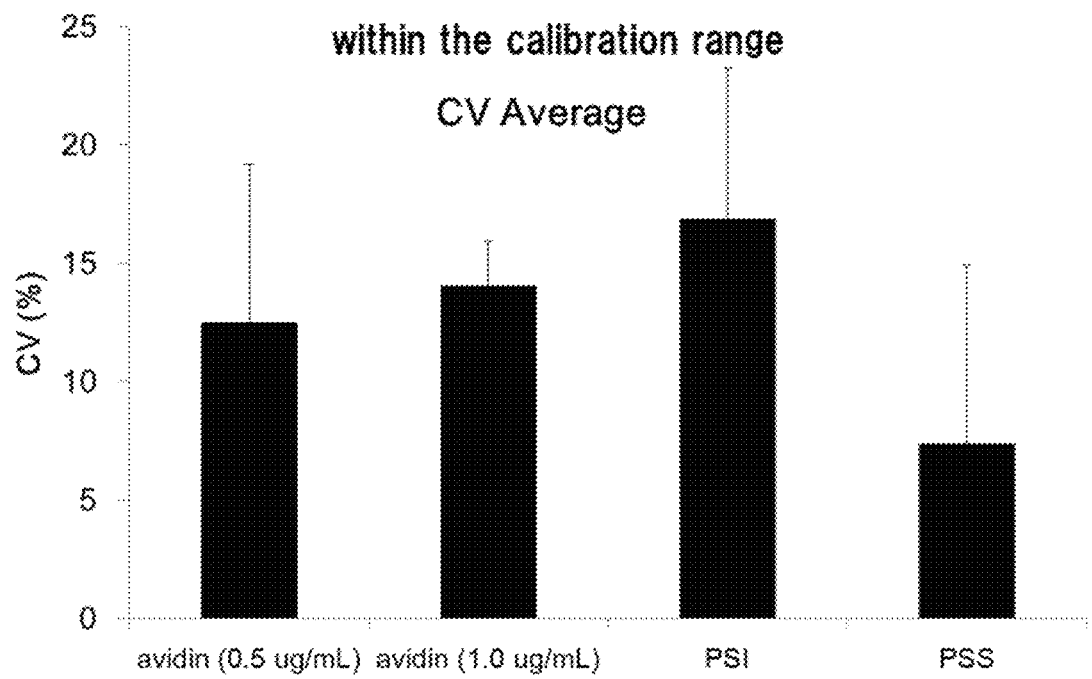

[FIG. 25]
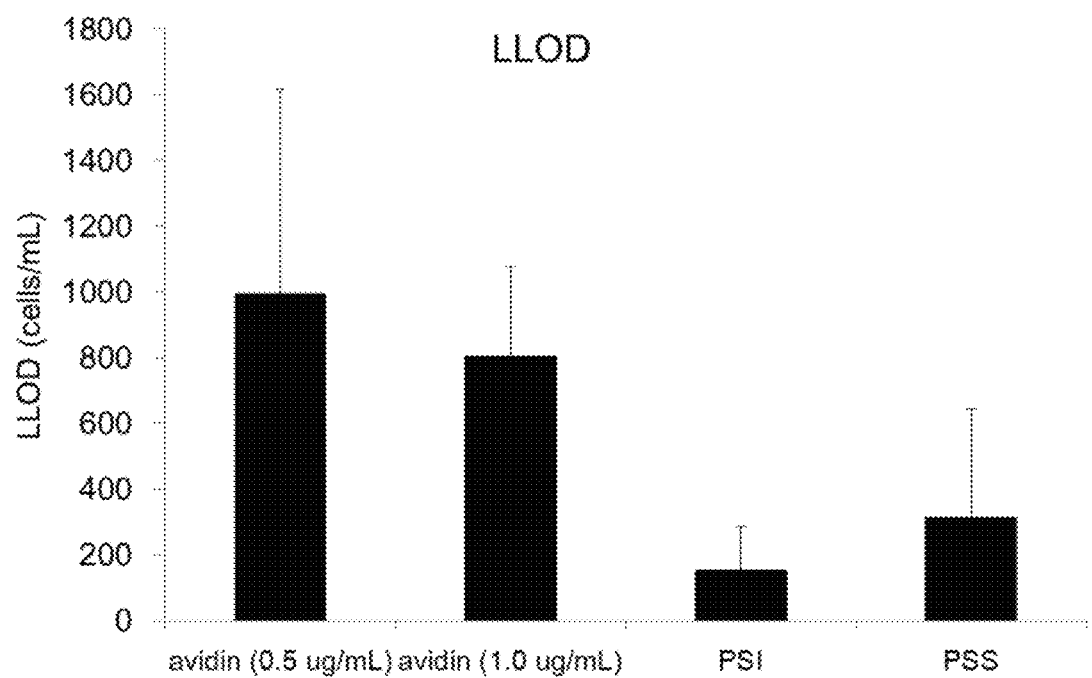

[FIG. 26]
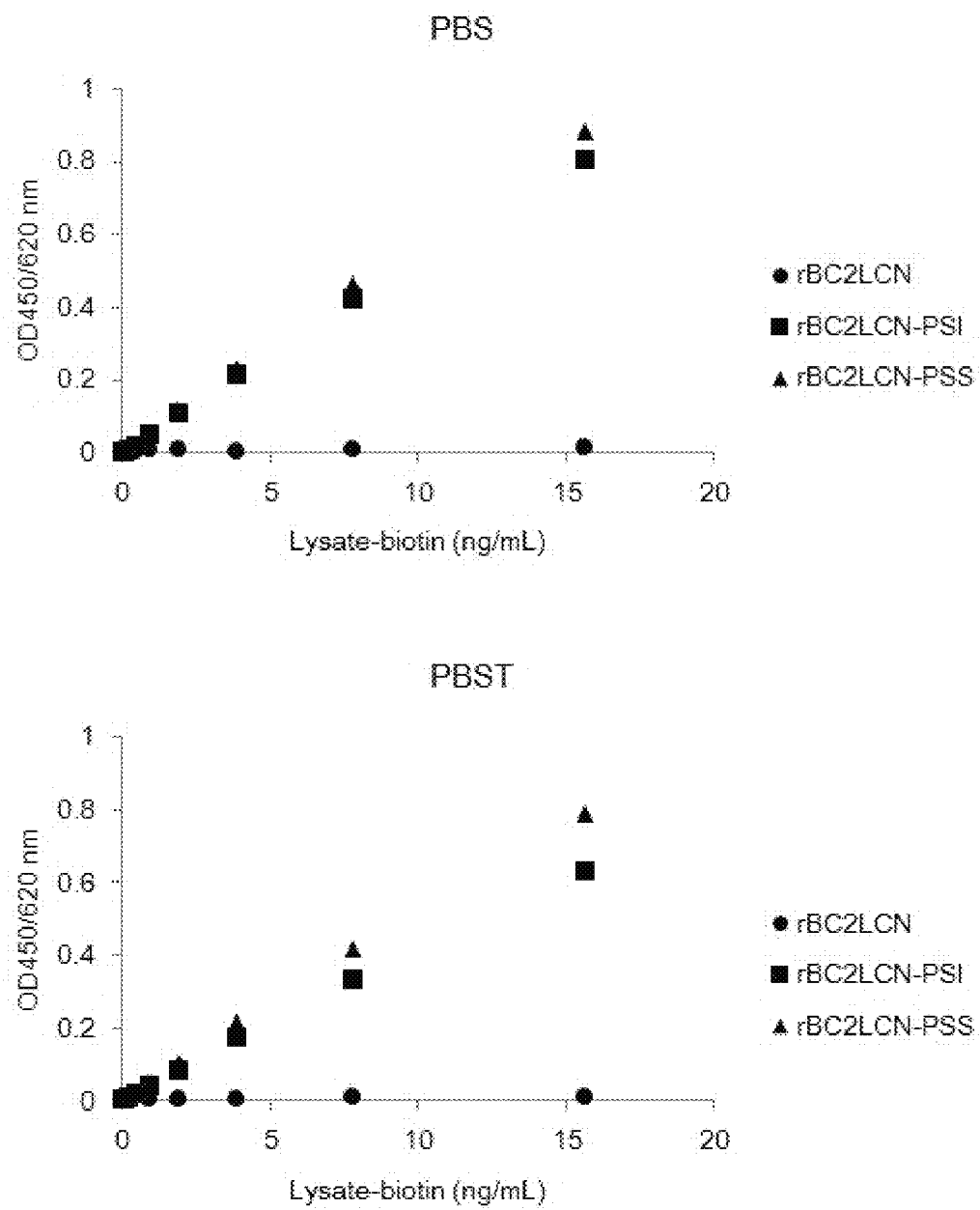

[FIG. 27]
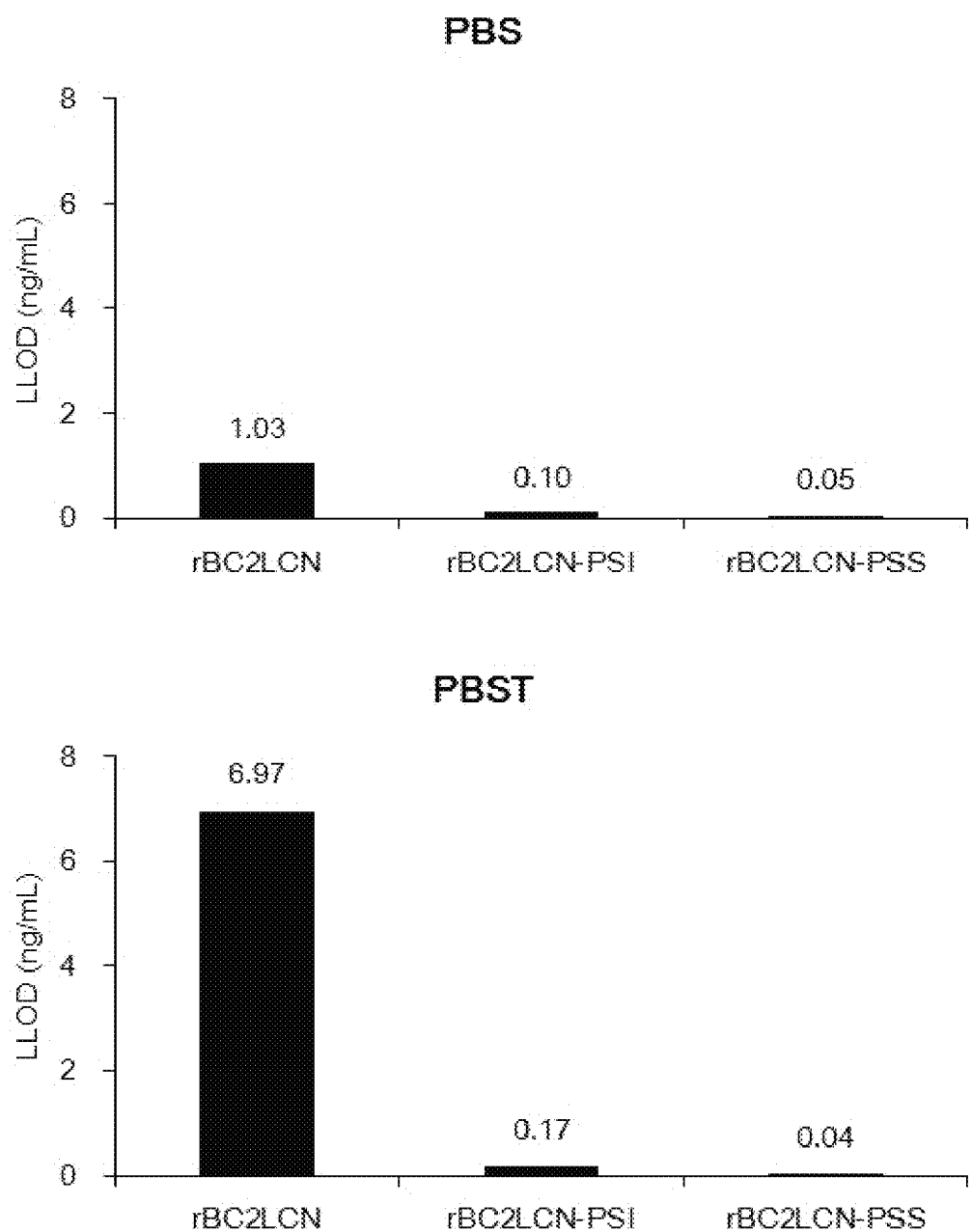

[FIG. 28]
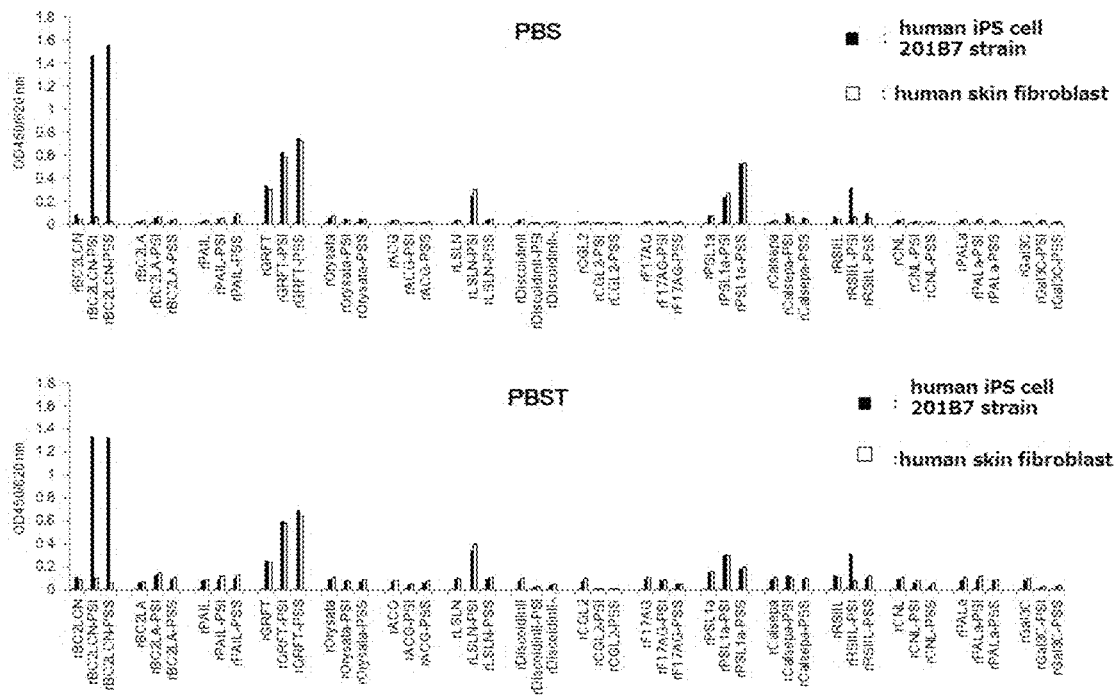
[FIG. 29]
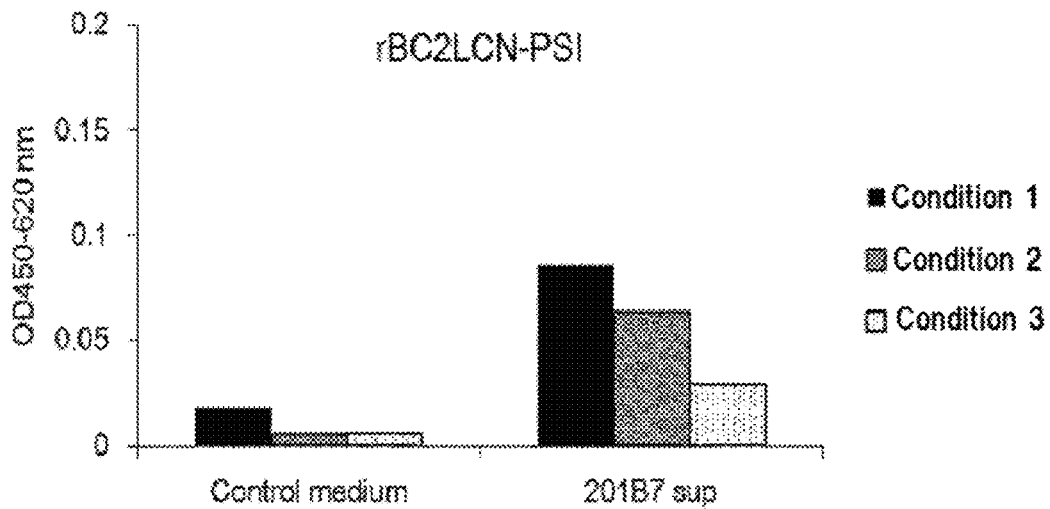

[FIG. 30]
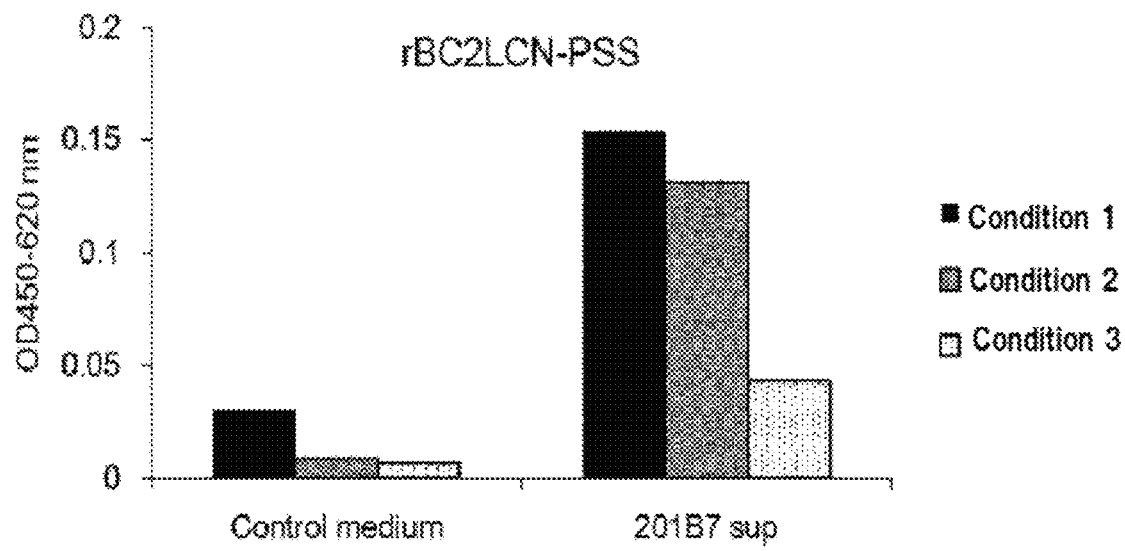
[FIG. 31]
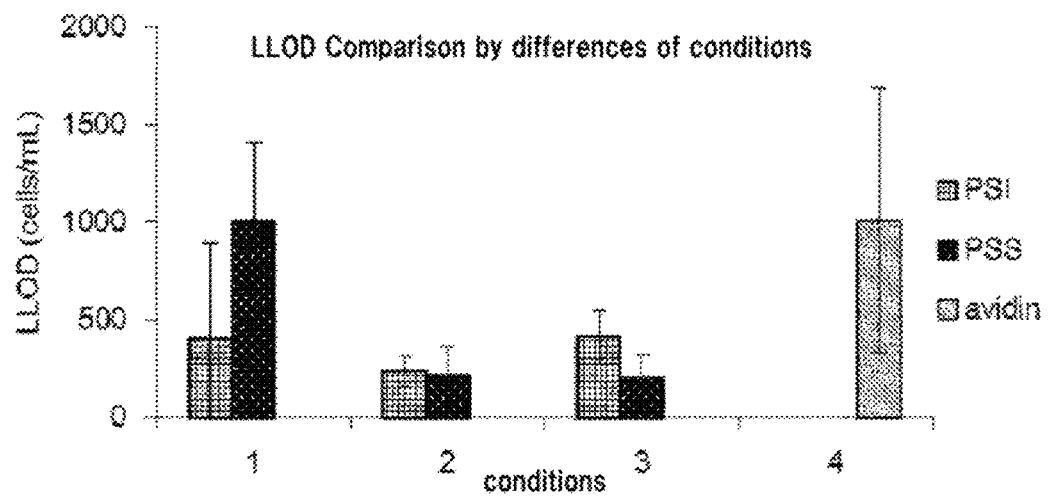

[FIG. 32]
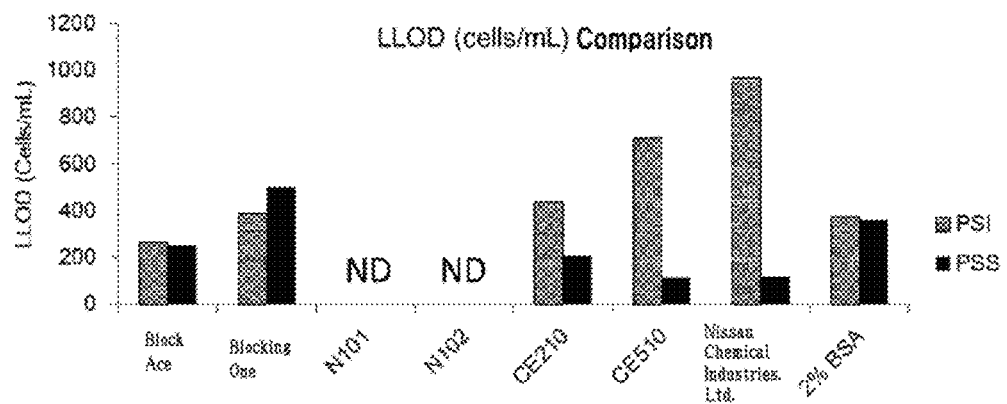
[FIG. 33]
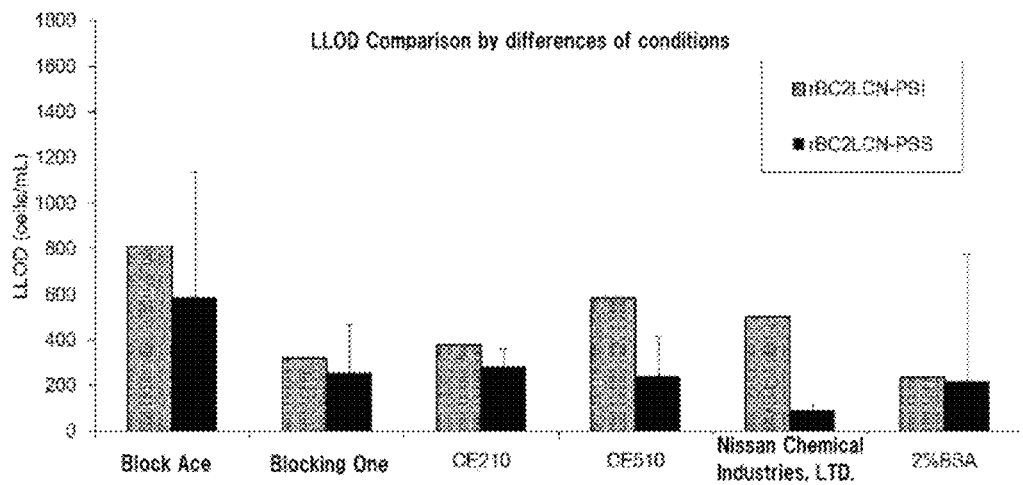

SEQUENCE LISTING

```
<160> NUMBER OF SEQ ID NOS: 25

<210> SEQ ID NO 1
<211> LENGTH: 9
<212> TYPE: PRT
<213> ORGANISM: Artificial Sequence
<220> FEATURE:
<223> OTHER INFORMATION: PS-tag
<220> FEATURE:
<221> NAME/KEY: VARIANT
<222> LOCATION: (2)..(2)
<223> OTHER INFORMATION: Xaa= Ile, Leu, Val, Ala, Gly, Met, Ser or Thr
<220> FEATURE:
<221> NAME/KEY: VARIANT
<222> LOCATION: (3)..(3)
<223> OTHER INFORMATION: Xaa= Ile, Leu, Val, Ala, Gly, Met, Ser or Thr
<220> FEATURE:
<221> NAME/KEY: VARIANT
<222> LOCATION: (4)..(4)
<223> OTHER INFORMATION: Xaa= Ile, Leu, Val, Ala, Gly, Met, Ser or Thr
<220> FEATURE:
<221> NAME/KEY: VARIANT
<222> LOCATION: (7)..(7)
<223> OTHER INFORMATION: Xaa= Ile, Leu, Val, Ala, Gly, Met, Ser or Thr

<400> SEQUENCE: 1

Arg Xaa Xaa Xaa Arg Arg Xaa Arg Arg
1               5

<210> SEQ ID NO 2
<211> LENGTH: 9
<212> TYPE: PRT
<213> ORGANISM: Artificial Sequence
<220> FEATURE:
<223> OTHER INFORMATION: PS-tag(PSI)

<400> SEQUENCE: 2

Arg Ile Ile Ile Arg Arg Ile Arg Arg
1               5

<210> SEQ ID NO 3
<211> LENGTH: 9
<212> TYPE: PRT
<213> ORGANISM: Artificial Sequence
<220> FEATURE:
<223> OTHER INFORMATION: PS-tag(PSA/I)

<400> SEQUENCE: 3

Arg Ala Ile Ala Arg Arg Ile Arg Arg
1               5
```

```
<210> SEQ ID NO 4
<211> LENGTH: 9
<212> TYPE: PRT
<213> ORGANISM: Artificial Sequence
<220> FEATURE:
<223> OTHER INFORMATION: PS-tag(PSL)

<400> SEQUENCE: 4

Arg Leu Leu Leu Arg Arg Leu Arg Arg
1               5

<210> SEQ ID NO 5
<211> LENGTH: 9
<212> TYPE: PRT
<213> ORGANISM: Artificial Sequence
<220> FEATURE:
<223> OTHER INFORMATION: PS-tag(PSV)

<400> SEQUENCE: 5

Arg Val Val Val Arg Arg Val Arg Arg
1               5

<210> SEQ ID NO 6
<211> LENGTH: 9
<212> TYPE: PRT
<213> ORGANISM: Artificial Sequence
<220> FEATURE:
<223> OTHER INFORMATION: PS-tag(PSA)

<400> SEQUENCE: 6

Arg Ala Ala Ala Arg Arg Ala Arg Arg
1               5

<210> SEQ ID NO 7
<211> LENGTH: 9
<212> TYPE: PRT
<213> ORGANISM: Artificial Sequence
<220> FEATURE:
<223> OTHER INFORMATION: PS-tag(PSG)

<400> SEQUENCE: 7

Arg Gly Gly Gly Arg Arg Gly Arg Arg
1               5

<210> SEQ ID NO 8
<211> LENGTH: 9
<212> TYPE: PRT
<213> ORGANISM: Artificial Sequence
<220> FEATURE:
<223> OTHER INFORMATION: PS-tag(PSM)

<400> SEQUENCE: 8

Arg Met Met Met Arg Arg Met Arg Arg
1               5

<210> SEQ ID NO 9
<211> LENGTH: 9
<212> TYPE: PRT
<213> ORGANISM: Artificial Sequence
<220> FEATURE:
<223> OTHER INFORMATION: PS-tag(PSS)

<400> SEQUENCE: 9

Arg Ser Ser Ser Arg Arg Ser Arg Arg
1               5

<210> SEQ ID NO 10
```

```
<211> LENGTH: 9
<212> TYPE: PRT
<213> ORGANISM: Artificial Sequence
<220> FEATURE:
<223> OTHER INFORMATION: PS-tag(PST)

<400> SEQUENCE: 10

Arg Thr Thr Thr Arg Arg Thr Arg Arg
1               5

<210> SEQ ID NO 11
<211> LENGTH: 12
<212> TYPE: PRT
<213> ORGANISM: Artificial Sequence
<220> FEATURE:
<223> OTHER INFORMATION: PS-tag

<400> SEQUENCE: 11

Lys Gly Leu Arg Gly Trp Arg Glu Met Ile Ser Leu
1               5                   10

<210> SEQ ID NO 12
<211> LENGTH: 12
<212> TYPE: PRT
<213> ORGANISM: Artificial Sequence
<220> FEATURE:
<223> OTHER INFORMATION: PS-tag

<400> SEQUENCE: 12

Ala Asp Tyr Leu Ser Arg Trp Gly Ser Ile Arg Asn
1               5                   10

<210> SEQ ID NO 13
<211> LENGTH: 12
<212> TYPE: PRT
<213> ORGANISM: Artificial Sequence
<220> FEATURE:
<223> OTHER INFORMATION: PS-tag

<400> SEQUENCE: 13

Ser Arg Val His Arg Ala Val Leu Asn Gly Val Ser
1               5                   10

<210> SEQ ID NO 14
<211> LENGTH: 12
<212> TYPE: PRT
<213> ORGANISM: Artificial Sequence
<220> FEATURE:
<223> OTHER INFORMATION: PS-tag

<400> SEQUENCE: 14

Arg Pro Pro Gly Val Val Arg Arg Tyr Ala Leu Gly
1               5                   10

<210> SEQ ID NO 15
<211> LENGTH: 12
<212> TYPE: PRT
<213> ORGANISM: Artificial Sequence
<220> FEATURE:
<223> OTHER INFORMATION: PS-tag

<400> SEQUENCE: 15

Val Arg Ser Trp Glu Glu Gln Ala Arg Val Thr Thr
1               5                   10

<210> SEQ ID NO 16
<211> LENGTH: 12
```

```
<212> TYPE: PRT
<213> ORGANISM: Artificial Sequence
<220> FEATURE:
<223> OTHER INFORMATION: PS-tag

<400> SEQUENCE: 16

Arg Ala Phe Ile Ala Ser Arg Arg Ile Lys Arg Pro
1               5                   10

<210> SEQ ID NO 17
<211> LENGTH: 12
<212> TYPE: PRT
<213> ORGANISM: Artificial Sequence
<220> FEATURE:
<223> OTHER INFORMATION: PS-tag

<400> SEQUENCE: 17

Arg Glu Ser Thr Leu Lys Gly Thr Ser Arg Ala Val
1               5                   10

<210> SEQ ID NO 18
<211> LENGTH: 12
<212> TYPE: PRT
<213> ORGANISM: Artificial Sequence
<220> FEATURE:
<223> OTHER INFORMATION: PS-tag

<400> SEQUENCE: 18

Ala Gly Leu Arg Leu Lys Lys Ala Ala Ile His Arg
1               5                   10

<210> SEQ ID NO 19
<211> LENGTH: 12
<212> TYPE: PRT
<213> ORGANISM: Artificial Sequence
<220> FEATURE:
<223> OTHER INFORMATION: PS-tag

<400> SEQUENCE: 19

Ser Ser Leu Leu Arg Ala Val Pro Glu Pro Thr Gly
1               5                   10

<210> SEQ ID NO 20
<211> LENGTH: 12
<212> TYPE: PRT
<213> ORGANISM: Artificial Sequence
<220> FEATURE:
<223> OTHER INFORMATION: PS-tag

<400> SEQUENCE: 20

Arg Ala Phe Ile Ala Ser Arg Arg Ile Arg Arg Pro
1               5                   10

<210> SEQ ID NO 21
<211> LENGTH: 24
<212> TYPE: PRT
<213> ORGANISM: Artificial Sequence
<220> FEATURE:
<223> OTHER INFORMATION: PMMA-tag(PMOMP25)

<400> SEQUENCE: 21

Asp Val Glu Gly Ile Gly Asp Val Asp Leu Val Asn Tyr Phe Glu Val
1               5                   10                  15

Gly Ala Thr Tyr Tyr Phe Asn Lys
            20
```

-continued

```
<210> SEQ ID NO 22
<211> LENGTH: 30
<212> TYPE: PRT
<213> ORGANISM: Artificial Sequence
<220> FEATURE:
<223> OTHER INFORMATION: SiN-tag(V821)

<400> SEQUENCE: 22

Gly Gly Arg His Thr Pro Phe Phe Lys Gly Tyr Arg Pro Gln Phe Tyr
1               5                   10                  15

Phe Arg Thr Thr Asp Val Thr Gly Thr Ile Glu Leu Pro Glu
            20                  25                  30

<210> SEQ ID NO 23
<211> LENGTH: 30
<212> TYPE: PRT
<213> ORGANISM: Artificial Sequence
<220> FEATURE:
<223> OTHER INFORMATION: PDMS-tag(ELN-V81)

<400> SEQUENCE: 23

Met Val Met Pro Gly Asp Asn Ile Lys Met Val Val Thr Leu Ile His
1               5                   10                  15

Pro Ile Ala Met Asp Asp Gly Leu Arg Phe Ala Ile Arg Glu
            20                  25                  30

<210> SEQ ID NO 24
<211> LENGTH: 156
<212> TYPE: PRT
<213> ORGANISM: Artificial Sequence
<220> FEATURE:
<223> OTHER INFORMATION: rBC2LCN

<400> SEQUENCE: 24

Met Pro Leu Leu Ser Ala Ser Ile Val Ser Ala Pro Val Val Thr Ser
1               5                   10                  15

Glu Thr Tyr Val Asp Ile Pro Gly Leu Tyr Leu Asp Val Ala Lys Ala
            20                  25                  30

Gly Ile Arg Asp Gly Lys Leu Gln Val Ile Leu Asn Val Pro Thr Pro
        35                  40                  45

Tyr Ala Thr Gly Asn Asn Phe Pro Gly Ile Tyr Phe Ala Ile Ala Thr
    50                  55                  60

Asn Gln Gly Val Val Ala Asp Gly Cys Phe Thr Tyr Ser Ser Lys Val
65                  70                  75                  80

Pro Glu Ser Thr Gly Arg Met Pro Phe Thr Leu Val Ala Thr Ile Asp
                85                  90                  95

Val Gly Ser Gly Val Thr Phe Val Lys Gly Gln Trp Lys Ser Val Arg
            100                 105                 110

Gly Ser Ala Met His Ile Asp Ser Tyr Ala Ser Leu Ser Ala Ile Trp
        115                 120                 125

Gly Thr Ala Ala Pro Ser Ser Gln Gly Ser Gly Asn Gln Gly Ala Glu
    130                 135                 140

Thr Gly Gly Thr Gly Ala Gly Asn Ile Gly Gly Gly
145                 150                 155

<210> SEQ ID NO 25
<211> LENGTH: 9
<212> TYPE: PRT
<213> ORGANISM: Artificial Sequence
<220> FEATURE:
<223> OTHER INFORMATION: FLAG-tag
```

```
<400> SEQUENCE: 25

Asp Tyr Lys Asp Asp Asp Asp Lys His
1               5
```

METHOD FOR IMMOBILIZING LECTIN

CROSS-REFERENCE TO RELATED APPLICATION

This application is a U.S. National Stage entry under 35 U.S.C. § 371 of International Application No. PCT/JP2018/015163, filed on Apr. 11, 2018, which claims priority to Japanese Patent Application No. 2017-078414, filed on Apr. 11, 2017.

SEQUENCE LISTING

The instant application contains a Sequence Listing which has been submitted electronically in ASCII format and is hereby incorporated by reference in its entirety. Said ASCII copy, created on Feb. 9, 2021, is named 048318-679N01US_Sequence Listing.txt and is 7,375 bytes in size.

TECHNICAL FIELD

The present invention relates to a base material on which lectin is immobilized, a method for immobilizing lectin on a base material, and a method for detecting, measuring, or separating a target sugar chain, a target glycoconjugate, a cell having a target glycoconjugate, an extracellular vesicle, a virus, or the like (hereinafter, these are each collectively also referred to as a "target sugar chain-containing antigen") by using the base material.

BACKGROUND ART

A surface of a living cell is covered with a sugar chain, and it is considered that the cell exchanges information with other cells via the sugar chain, and a sugar chain structure on a surface of a cell changes in response to the change of a state of the cell in various scenes such as a developmental stage of an organism, life activities, pathogen infection, and canceration. Therefore, by analyzing the sugar chain on a surface of a cell, it is possible to know the differentiation level of the cell, the presence or absence of cancer or pathogens, the severity of disease, and the like. Further, also in drug development for cancer or various kinds of diseases, analysis of a sugar chain antigen is important as a therapeutic target, or for elucidating the cause of side effects and the like.

In recent years, the research and development of a lectin-lectin sandwich method and a lectin-antibody sandwich method, which target a glycoconjugate on a surface of a cell containing a specific target sugar chain, an extracellular vesicle, or a virus, or a glycoconjugate secreted into a body fluid such as blood has been actively conducted.

In particular, recently, focusing on a phenomenon that a sugar chain on a specific glycoprotein changes in response to the change in a disease state, a large number of techniques for quantifying the change in the sugar chain content by such a sandwich assay have been proposed. For example, diagnostic techniques for various kinds of diseases, such as detection of a surface marker for epithelial ovarian cancer that includes ceruloplasmin containing an *Aleuria aurantia* lectin (AAL) and/or *Wisteria floribunda* agglutinin (WFA) lectin-binding sugar chain (JP 5906447 B2) developed by National Institute of Advanced Industrial Science and Technology, Independent Administrative Agency; diagnosis by a body fluid of idiopathic normal pressure hydrocephalus that includes transferrin containing a *Psathyrella velutina* lectin (PVL) and/or *Sambucus sieboldiana* agglutinin (SSA) lectin-binding sugar chain (JP 5696273 B2); detection of a surface marker for WFA-binding glycoprotein intrahepatic cholangiocarcinoma (JP 5787389 B2); and detection of a liver-disease pathological index sugar chain marker that includes a lectin-binding M2BP glycoprotein such as WFA and *Bauhinia purpurea* (BPL) (JP 5031928 B2) can be mentioned.

In addition, the present inventors, et al. have found for a long time that BC2LCN is a lectin that can specifically recognize an undifferentiated sugar chain marker "Fucα1-2Galβ1-3GlcNAc" and/or "Fucα1-2Galβ1-3GalNAc" on a surface of a stem cell such as an induced pluripotent stem (iPS) cell, further, have found that the undifferentiation degree of a stem cell can be determined by measuring the BC2LCN-specific sugar chain contained in podocalyxin even in the culture supernatant, and have developed a lectin-lectin sandwich method and a lectin-antibody sandwich enzyme-linked immunosorbent assay (ELISA) method, for determining the undifferentiation degree in a culture supernatant of a stem cell by using a BC2LCN lectin probe (Patent Document 1).

At the same time, the present inventors, et al. have also developed a stem cell concentration technique using a BC2LCN-immobilized carrier by utilizing the specificity of a BC2LCN undifferentiated sugar chain marker, and a technique for separating and removing undifferentiated cells from a culture medium of stem cells after differentiation treatment, such as a living donor organ transplantation material (Patent Document 2).

As described above, the importance of a lectin-lectin or lectin-antibody sandwich assay technique for accurately and easily measuring the binding amount of lectin and a sugar chain is increasing more and more.

Further, if it is possible to provide an easy-to-handle lectin plate such as an antibody plate for immunoassay, which has already been put into practical use for antibodies, and with which target antigen markers of various cancers, pathogens and the like can be easily tested, and the diagnosis can be easily made, the rapidity and accuracy of diagnosis in medical practice will be greatly improved.

However, in general, the interaction between lectin and a sugar chain is extremely low, and it is considered that the constant of binding is 100 to 10,000 times smaller than that of antigen-antibody reaction (in general, the binding constant of antigen-antibody reaction is considered to be $10^{6-9}$ $M^{-1}$, whereas the binding constant between lectin and a sugar chain is considered to be $10^{4-7} M^{-1}$). Therefore, in many cases, sufficient washing cannot be performed for the lectin bound to a target sugar chain antigen, and a fluorescence detection device for common ELISA and a detection device for immunoassay have a high background, and thus it has been difficult to perform the accurate measurement. If a scanner by utilizing an evanescent wave excitation fluorescence detection method, which has been developed by National Institute of Advanced Industrial Science and Technology, Independent Administrative Agency, is used, washing operation is not required, and weak interaction between a sugar chain and lectin in a sample can be detected, and therefore, accurate quantification can also be realized, however, the device is large in size and expensive, and has not yet been a commonly-spread measurement device in the fields of medical care and research. Moreover, it is not suitable for the measurement of a simple lectin plate for diagnosis, which can be immediately determined even by visual observation.

As a method for immobilizing lectin on a surface of a base material such as a plate, there is a direct method of immobilizing lectin directly on a plate, however, a biotin-avidin indirect method in which lectin is biotinylated, and the biotinylated lectin or a commercially available biotinylated lectin is immobilized on an avidin-coated plate is widely used because of the high sensitivity. However, in a case of a biotinylated lectin plate, there has been a problem that the quality is not stable because of the variation in every lot.

Accordingly, there has been a strong desire to provide a lectin plate on which lectin capable of recognizing sugar chain antigens that serves as various kinds of sugar chain markers is immobilized, and which is a highly-sensitive lectin plate with stable quality capable of being applied widely to a lectin-lectin or lectin-antibody sandwich assay.

CITATION LIST

Patent Document

Patent Document 1: WO 2013/065302
Patent Document 2: WO 2013/128914
Patent Document 3: JP 5553336 B2
Patent Document 4: JP 5655254 B2
Patent Document 5: WO 2013/122061
Patent Document 6: WO 2016/129695
Patent Document 7: JP 5851391 B2

Non-Patent Document

Non-Patent Document 1: Kumada, Y., et al., Biotechnol. Prog., 22(2), 401-5 (2006)
Non-Patent Document 2: Kumada, Y., et al., J. Immunol. Methods., 385, 15-22 (2012)

SUMMARY OF THE INVENTION

Problems to be Solved by the Invention

An object of the present invention is to provide a highly-sensitive and less-expensive lectin plate with stable quality capable of being sufficiently washed after being bound to a target sugar chain-containing antigen as in the case of an antibody plate, and to provide a method for immobilizing lectin to produce the lectin plate.

Means for Solving the Problems

As an immobilization technique for achieving the high density by aligning orientation of a protein probe having a target recognition site on one side, such as a single-chain antibody, on a surface of the carrier, the present inventors, et al. have previously developed a peptide group capable of specifically adsorbing to each of various kinds of carriers for immobilization (Patent Documents 3 to 6).

In particular, in a low-molecular antibody such as a single-chain antibody, a high affinity specific for a target antigen can be exhibited by immobilizing the antibody on a base material surface, with high density and high orientation by the method (Non-Patent Document 1, and Patent Document 7).

In this regard, in the present specification, a peptide group having an affinity mainly for a hydrophilic polystyrene resin, which is described in Patent Document 3, is referred to as a "PS tag", a peptide group having an affinity for a polycarbonate resin and/or a polymethyl methacrylate resin, which is described in Patent Document 4, is referred to as a "PMMA/PC tag", a peptide group having an affinity for silicon nitride ($Si_3N_4$), which is described in Patent Document 5, is referred to as a "SiN tag", and a peptide group having an affinity for poly dimethylsiloxane (PDMS), which is described in Patent Document 6, is referred to as a "PDMS tag".

Further, the methods for binding these tag genes to lectin genes are the same as each other, and the methods for expressing tagged lectin from host cells by expression vectors are also the same as each other, and the adsorption methods to solid phases are nearly common to each other, and therefore, the "PS tag" will be mainly described. That is, when a "PS tag" is described in the present invention, the "PS tag" may refer to the whole "tags for immobilizing lectin" of the present invention, including a "PMMA/PC tag", a "SiN tag, and a "PDMS tag".

When the present inventors, et al. have conducted intensive studies on the production of a highly-sensitive lectin plate with stable quality, it has been conceived to use these peptide groups developed by the present inventors, et al. as the tags for immobilization.

However, in a case of lectin, different from the case of a single-chain antibody, lectin is a protein having a bulky and complicated dimensional structure and various charge states on the surface, and therefore, it has been unknown how densely lectin can be immobilized, and it has also been unclear whether or not the densification is effective in the first place. Further, since lectin usually has multiple target recognition sites by the multimerization, it has been unclear whether or not the affinity is improved by orientation control.

The present inventors have first selected BC2LCN (SEQ ID NO: 24) capable of recognizing an undifferentiated sugar chain marker, as a lectin, and have investigated the combination of a typical PS tag described in Patent Document 3 or the like and an affinity polystyrene plate as a tag for immobilization and a carrier for immobilization. By using a PSI tag (RIIIRRIRR: SEQ ID NO: 2) and a PSS tag (RSSSRRSRR: SEQ ID NO: 9) as the PS tags, four kinds of BC2LCN-PS tags, in which a PSI tag or a PSS tag is bound to the N-terminal side or C-terminal side of a BC2LCN lectin, were produced by utilizing a gene recombination technique.

As a result, in a case of the BC2LCN lectin, the yield of the BC2LCN-PSS tag in which a PSS tag is bound to the C-terminal side of the lectin was the highest. In a similar manner, when also other 14 kinds of recombinant lectins each expressed so that a PSI tag or a PSS tag is bound to the C-terminal side, the yield of each of the PSS-tagged lectins was high in all of the lectins except for a rBambL lectin, and therefore, it has been suggested that the efficacy of the PSS tag is generally high as a PS tag in a case of a recombinant lectin. Further, at the same time, as in the case of the rBambL lectin, the binding ability is not increased with a PSS tag, however, if a PSI tag is used, improvement in the binding ability may be observed, and therefore, it has been found that a PS tag has compatibility in response to the kind of lectin. That is, it has been also found that a PS tag having good compatibility is only necessary to be selected as appropriate in response to the kind of the lectin to be immobilized.

Next, when a BC2LCN lectin plate oriented in high density is prepared by making the C-terminal side of a BC2LCN lectin to be PSS tagged or PSI tagged, and adsorbing the BC2LCN lectin to a polystyrene plate modified to have high hydrophilicity, a uniform plate can be provided, and the uniform plate can withstand sufficient washing. As compared with a plate to be used for immobilization in a system of biotin-avidin, a PSS/PSI-tagged lectin plate exerts a noticeable effect that a uniform plate with no difference between the lots can be produced, in addition to an advantage that the labor and cost for avidin-coating a plate in advance are not required.

The obtained PSS/PSI-tagged BC2LCN lectin plate is applied to an ELISA method to detect an undifferentiated cell sugar chain marker in an iPS cell culture supernatant, and when the results are compared with the detection results by a conventional biotin-avidin binding plate, the high reactivity (detection sensitivity) equal to or higher than that in a case of the biotin-avidin binding plate and the low detection limit value have been able to be achieved. Further, it has also been able to be confirmed that by selecting a blocking agent and optimizing the blocking conditions, the detection limit value can be significantly lowered and the data variation can be reduced.

In addition, when the reactivity with a human iPS cell and the detection limit value have been examined, a high reactivity and a low detection limit value have been able to be achieved.

For also other multiple lectins, a uniform lectin plate with high density has been able to be provided by PSS tagging or PSI tagging. The similar high reactivity and low detection limit value can be expected also for these lectins.

Further, it has been strongly suggested that in response to the kind of lectin, the affinity for a solid phase can be increased by binding a PS tag other than the PSS tag or PSI tag. In addition, it has been also suggested that a "PMMA/PC tag" can be used in a case where the solid phase is a polycarbonate or polymethyl methacrylate resin, a "SiN tag" can be used in a case where the solid phase is silicon nitride ($Si_3N_4$), and a "PDMS tag" can be used in a case where the solid phase is polydimethylsiloxane.

The present invention has been completed by obtaining the above experimental results.

In the present invention, fusions of various kinds of lectins and tag peptides such as "PS tags" are also simply referred to as "lectin-peptide fusions" or "tagged lectins".

That is, the present invention includes the following invention.

[1] A lectin-peptide fusion, including: a peptide capable of adsorbing to a base material surface; and a lectin capable of recognizing a target sugar chain, in which the peptide is provided on an N-terminal side or a C-terminal side of the lectin.

[2] The fusion described in [1], in which the peptide is a peptide selected from the group consisting of a PS peptide, a PMMA/PC peptide, a SiN peptide, and a PDMS peptide.

[3] The fusion described in [1] or [2], in which the lectin is a lectin selected from the group consisting of a rACG lectin, a rPSL1a lectin, a rLSLN lectin, a rDiscoidin I lectin, a rDiscoidin II lectin, a rCGL2 lectin, a rSRL lectin, a rF17AG lectin, a rGRFT lectin, a rOrysata lectin, a rCalsepa lectin, a rBC2LA lectin, a rAAL lectin, a rPAIIL lectin, a rRSIIL lectin, a rPPL lectin, a rCNL lectin, a rPAIL lectin, a rABA lectin, a rMOA lectin, a rPALa lectin, a rGal3CS lectin, a rMpL lectin, a rAAL2 lectin, a rBambL lectin, and a rPVL lectin.

[4] The fusion described in any one of [1] to [3], in which the peptide is a peptide containing any one of amino acid sequences shown in SEQ ID NOs: 1 to 23.

[5] The fusion described in any one of [2] to [4], in which the peptide is a PS peptide including a PSI tag having an amino acid sequence of SEQ ID NO: 2, or a PSS tag having an amino acid sequence of SEQ ID NO: 9.

[6] The fusion described in any one of [1] to [5], in which an amino acid sequence of lectin and/or peptide constituting the lectin-peptide fusion includes an amino acid sequence with deletion, substitution, insertion, or addition of amino acid residues in an amount of less than 10% relative to the total amino acid residues of each amino acid sequence of the lectin and peptide.

[7] A lectin-peptide fusion gene, including a nucleic acid sequence encoding the amino acid sequence described in [6].

[8] A vector capable of expressing a lectin-peptide fusion, including the lectin-peptide fusion gene described in [7].

[9] An immobilized lectin-peptide fusion, including: the lectin-peptide fusion described in any one of [1] to [6]; and a base material, in which a peptide side in the lectin-peptide fusion is immobilized on the base material.

[10] A base material, on which the lectin-peptide fusion described in any one of [1] to [6] is immobilized.

In this regard, for example, in a case where the peptide fused with a lectin is a PS tag such as a PSI tag, or a PSS tag, as the base material, a base material made of a resin having a hydrophilic surface, and particularly a resin plate, is preferred. In that case, it can be expressed as follows.

A base material, including a resin plate having a hydrophilic surface on which the lectin-PS tag fusion described in [5] or [6] is immobilized.

[11] A method for measuring or isolating a target sugar chain-containing antigen, including a process of bringing a sample containing a target sugar chain-containing antigen into contact with the base material described in [10].

[12] The method described in [11], further including a process of overlaying an antibody capable of recognizing the target sugar chain-containing antigen.

[13] The method described in [12], in which in the process of overlaying an antibody capable of recognizing the target sugar chain-containing antigen, a blocking agent is contained in a diluent for a base material on which a lectin-peptide fusion is immobilized, and/or a diluent for an antibody.

[14] The method described in [12] or [13], in which the target sugar chain-containing antigen is a sugar chain-containing antigen contained in a solution containing contaminants derived from a test sample.

[15] A method for concentrating a cell having a target sugar chain or a glycoconjugate, including: a process of allowing a sample containing a cell having a target sugar chain on a surface of the cell or a glycoconjugate having a target sugar chain to adsorb to the base material described in [10]; and a process of harvesting a target sugar chain-containing substance.

[16] A kit or device for measuring or isolating a target sugar chain-containing antigen, including the base material described in [10].

[17] The kit or device described in [16], further including an antibody capable of recognizing the target sugar chain-containing antigen.

[18] A method for producing a base material on which a lectin-peptide fusion is immobilized, including a process of bringing the lectin-peptide fusion described in any one of [1] to [6] into contact with a base material.

[19] The production method described in [18], in which the process of bringing the lectin-peptide fusion into contact with a base material is performed in a buffer solution.

[20] The production method described in [19], in which the buffer solution has a pH of 6.5 to 7.5.

[21] The production method described in [19] or [20], in which the buffer solution has a salt concentration of 0.10 to 0.20 M.

Advantageous Effects of Invention

According to the present invention, by providing a highly-sensitive uniformly-oriented lectin plate with high density at a low cost, it has become possible to easily perform a lectin-lectin sandwich assay and a lectin-antibody sandwich assay with higher accuracy. Since a glycoconjugate containing a target sugar chain marker can be detected and measured easily, quickly, and accurately, the diagnosis of cancer and various kinds of diseases can be easily made with high accuracy also in medical practice.

Further, by using the uniformly-oriented lectin base material with high density of the present invention, a glycoprotein or cell containing a target sugar chain can be separated more quickly and accurately. For example, by utilizing the lectin base material in an isolation process of a stem cell, or various kinds of somatic cells differentiated from a stem cell, a safe transplantation material derived from a stem cell will be provided in the regenerative medicine area in future.

BRIEF DESCRIPTION OF DRAWINGS

FIG. 1 shows constructs of PSS-tagged rBC2LCN lectins and PSI-tagged rBC2LCN lectins.

FIG. 2 shows as follows: the rBC2LCN to which a PSI or PSS tag was added on the C-terminal side was expressed in *E. coli* and the expressed rBC2LCN was purified with fucose agarose; and in a case where the tag was added to the C-terminal side, 52 mg/L of PSI-tagged rBC2LCN, and 76 mg/L of PSS-tagged rBC2LCN were able to be purified.

FIG. 3 shows as follows: the rBC2LCN to which a PSI or PSS tag was added on the N-terminal side was expressed in *E. coli* and the expressed rBC2LCN was purified with fucose agarose; in a case where the tag was added to the N-terminal side, 4 mg/L of PSI-tagged rBC2LCN, and 1 mg/L of PSS-tagged rBC2LCN were only able to be purified; and it was found that the yield was higher when the tag was added on the C-terminal side of the lectin than that when the tag was added on the N-terminal side.

FIG. 4 shows as follows: various kinds of recombinant lectins such as rACG were also each expressed in recombinant *E. coli* so that the PSI tag or PSS tag was bound to the C-terminal side, the purification was performed with fucose agarose, and the yield of each of the PS-tagged lectins per liter of *E. coli* culture was measured; and as a result, it was found that the yield of the PSS-tagged lectin tended to be higher than that of the PSI-tagged lectin for almost all the lectins.

FIG. 5A shows as follows: untagged, PSI-tagged, and PSS-tagged rBC2LCN lectins were suspended in phosphate buffered saline (PBS), and the lectins suspended in PBS were allowed to react with various kinds of plates at various concentrations at room temperature for one hour; the washing with PBS with Tween 20 (PBST) was performed five times, and then the amount of adsorbed lectin was measured by a micro bicinchoninic acid (BCA) assay (ThemoFisher); at that time, as the plate, five kinds of plates, which are Nunc, Polysorp, and Maxisorp plates for ELISA, and further a carboplate and an AGC plate that had been treated to increase the surface hydrophilicity for PS tag were tested; and as a result, it was found that in a case where a PS tag was added, adsorption was observed, but adsorption on the least hydrophilic Polysorp plate was not favorable.

FIG. 5B shows as follows: untagged, PSI-tagged, and PSS-tagged rBC2LCN lectins were suspended in PBS with 0.1% Tween 20 (PBST), and similar operation as in FIG. 5A was performed by using the same plates as those in FIG. 5A; and as a result, even in a case where the PS tag was fused, adsorption was observed only on the higher hydrophilic carboplate and AGC plate.

FIG. 6 shows as follows: for the untagged, PSI-tagged, and PSS-tagged rAGC lectins, in a case of being suspended in PBS or PBST as in the case of rBC2LCN lectin, the rAGC lectins were allowed to react with various kinds of plates at room temperature for one hour, the washing with PBST was performed five times, and then the amount of adsorbed lectin was measured by a micro BCA assay (ThemoFisher); since the point where the effects of the high hydrophilic carboplate and AGC plate were high was similar to that in a case of the rBC2LCN lectin, the amount of adsorption of only the carboplate and AGC plate was shown in the drawing; and the same is applied to the following respective lectins.

FIG. 7 shows the amount of adsorption on each of the carboplate and the AGC plate at various concentrations in a case where untagged, PSI-tagged, and PSS-tagged rLSLN lectins were each suspended in PBS or PBST.

FIG. 8 shows the amount of adsorption on each of the carboplate and the AGC plate at various concentrations in a case where untagged, PSI-tagged, and PSS-tagged rDiscoidin II lectins were each suspended in PBS or PBST.

FIG. 9 shows the amount of adsorption on each of the carboplate and the AGC plate at various concentrations in a case where untagged, PSI-tagged, and PSS-tagged rCGL2 lectins were each suspended in PBS or PBST.

FIG. 10 shows the amount of adsorption on each of the carboplate and the AGC plate at various concentrations in a case where untagged, PSI-tagged, and PSS-tagged rF17AG lectins were each suspended in PBS or PBST.

FIG. 11 shows the amount of adsorption on each of the carboplate and the AGC plate at various concentrations in a case where untagged, PSI-tagged, and PSS-tagged rGRFT lectins were each suspended in PBS or PBST.

FIG. 12 shows the amount of adsorption on each of the carboplate and the AGC plate at various concentrations in a case where untagged, PSI-tagged, and PSS-tagged rOrysata lectins were each suspended in PBS or PBST.

FIG. 13 shows the amount of adsorption on each of the carboplate and the AGC plate at various concentrations in a case where untagged, PSI-tagged, and PSS-tagged rCalsepa lectins were each suspended in PBS or PBST.

FIG. 14 shows the amount of adsorption on each of the carboplate and the AGC plate at various concentrations in a case where untagged, PSI-tagged, and PSS-tagged rRSIIL lectins were each suspended in PBS or PBST.

FIG. 15 shows the amount of adsorption on each of the carboplate and the AGC plate at various concentrations in a case where untagged, PSI-tagged, and PSS-tagged rCNL lectins were each suspended in PBS or PBST.

FIG. 16 shows the amount of adsorption on each of the carboplate and the AGC plate at various concentrations in a case where untagged, PSI-tagged, and PSS-tagged rGal3C lectins were each suspended in PBS or PBST.

FIG. 17 shows the amount of adsorption on each of the carboplate and the AGC plate at various concentrations in a case where untagged, PSI-tagged, and PSS-tagged rPSL1a lectins were each suspended in PBS or PBST.

FIG. 18 shows the amount of adsorption on each of the carboplate and the AGC plate at various concentrations in a case where untagged, PSI-tagged, and PSS-tagged rPALa lectins were each suspended in PBS or PBST.

FIG. 19 shows the amount of adsorption on each of the carboplate and the AGC plate at various concentrations in a case where untagged, PSI-tagged, and PSS-tagged rBC2LA lectins were each suspended in PBS or PBST.

FIG. 20 shows the amount of adsorption on each of the carboplate and the AGC plate at various concentrations in a case where untagged, PSI-tagged, and PSS-tagged rPA1L lectins were each suspended in PBS or PBST.

FIG. 21 shows investigation of optimization conditions when lectin is immobilized, that is, the optimal pH range.

FIG. 22 shows investigation of optimization conditions when lectin is immobilized, that is, the optimal salt concentration.

FIG. 23 shows reactivity comparison of a PS-tagged lectin plate and an avidin plate (standard curve).

FIG. 24 shows comparison of the degrees of variation (variation constant: average value of CV) among PS-tagged lectin plates and avidin plates.

FIG. 25 shows comparison of the detection limit values among PS-tagged lectin plates and avidin plates.

FIG. 26 shows reactivity of a PSI- or PSS-tagged rBC2LCN with a hydrophobic fraction of human iPS cell 201B7 (PBS suspension).

FIG. 27 shows reactivity of a PSI- or PSS-tagged rBC2LCN with a hydrophobic fraction of human iPS cell 201B7 (PBST suspension).

FIG. 28 shows reactivity of various kinds of PSS/PSI-tagged lectins suspended in PBS or PBST with hydrophobic fractions of a human iPS cell 201B7 and a human skin fibroblast each immobilized on a carboplate.

FIG. 29 shows reactivity comparison of PSI-tagged lectin plates due to the difference in the blocking condition.

FIG. 30 shows reactivity comparison of PSS-tagged lectin plates due to the difference in the blocking condition.

FIG. 31 shows comparison of detection limit values of PS-tagged lectin plates due to the difference in the blocking condition.

FIG. 32 shows comparison of detection limit values of PS-tagged lectin plates due to the difference in the blocking agent (1).

FIG. 33 shows comparison of detection limit values of PS-tagged lectin plates due to the difference in the blocking agent (2).

DESCRIPTION OF EMBODIMENTS

1. Tag for Immobilizing Lectin Used in the Present Invention (1-1) Kind of Tag for Immobilizing Lectin Used in the Present Invention As the tag for immobilizing a lectin to be used in the present invention, a "PS tag" including a peptide group having an affinity for hydrophilic polystyrene, which has been developed previously by the present inventors, et al. (Patent Document 3), a "PMMA/PC tag" including a peptide group having an affinity for a polycarbonate resin and/or a polymethyl methacrylate resin (Patent Document 4), a "SiN tag" including a peptide group having an affinity for silicon nitride ($Si_3N_4$) (Patent Document 5), and a "PDMS tag" including a peptide group having an affinity for polydimethylsiloxane (Patent Document 6) are all included. According to a base material for immobilization and in consideration of the compatibility with the lectin to be used, the tag can be appropriately selected from these various kinds of peptide groups.

As described above, in a case where a tagged lectin fusion protein of the present invention is produced, the methods for binding to respective lectin genes are the same as each other, the methods for expressing respective tagged lectins each from a host cell by an expression vector are the same as each other, and the adsorption methods to respective solid phases are nearly common to each other, and therefore, in the present specification, as the tag for immobilization of the present invention, the "PS tag" will be mainly described, but the tag is not limited to a "PS tag".

Further, for the amino acid sequence of the tag for immobilizing lectin to be used in the present invention, deletion, substitution, addition, or insertion of amino acid residues is accepted as long as the amount of the residues to be deleted, substituted, added, or inserted is less than 10%, preferably less than 8%, and more preferably less than 5% within the range not impairing the adsorption ability for a solid phase (base material) in the amino acid sequences represented by respective SEQ ID Numbers, which are specifically shown below. In terms of the number of amino acid residues, the deletion, substitution, addition, or insertion of amino acid residues is accepted as long as the number of amino acid residues to be deleted, substituted, added, or inserted is, for example, 3 or less residues, for example, 2 or less residues, or for example, 1 residue. The position of the deletion, substitution, addition, or insertion at that time is preferably only the C-terminal or N-terminal of the tag.

(1-2) With Respect to PS Tag

The PS tag that can be used in the present invention refers to a peptide included in a peptide group that exerts a specific adsorption function on a surface of a solid phase having a hydrophilic resin surface, which has been described in Patent Document 3, and the PS tag is suitable particularly in a case where a polystyrene resin or polycarbonate resin whose surface hydrophilicity has been increased is used as a solid phase. The PS tag can be applied to the whole general polystyrene resins or polycarbonate resins as a solid phase for a sandwich assay with an antibody, such as a lectin array, an ELISA, or an immunoassay method.

Specifically, a peptide group shown as a peptide containing mainly an amino acid sequence of "RXXXRRXRR (in this regard, X is one of or a combination of multiple amino acid residues of I, L, V, A, G, M, S, and T): SEQ ID NO: 1", and for example, a peptide containing "RIIIRRIRR (SEQ ID NO: 2)", "RAIARRIRR (SEQ ID NO: 3)", "RLLLRRLRR (SEQ ID NO: 4)", "RVVVRRVRR (SEQ ID NO: 5)", "RAAARRARR (SEQ ID NO: 6)", "RGGGRRGRR (SEQ ID NO: 7)", "RMMMRRMRR (SEQ ID NO: 8)", "RSSSRRSRR (SEQ ID NO: 9)", or "RTTTRRTRR (SEQ ID NO: 10)".

In addition, a peptide containing "KGLRGWREMISL (SEQ ID NO: 11)", "ADYLSRWGSIRN (SEQ ID NO: 12)", "SRVHRAVLNGVS (SEQ ID NO: 13)", "RPPGVVRRYALG (SEQ ID NO: 14)", "VRSWEEQARVTT (SEQ ID NO: 15)", "RAFIASRRIKRP (SEQ ID NO: 16)", "RESTLKGTSRAV (SEQ ID NO: 17)", "AGLRLKKAAIHR (SEQ ID NO: 18)", "SSLLRAVPEPTG (SEQ ID NO: 19)", or "RAFIASRRIRRP (SEQ ID NO: 20)" also has an adsorption ability specific for a solid phase having a hydrophilic resin surface, similarly, and therefore, can also be similarly used as the "PS tag" of the present invention.

Among these PS tags, the preferred PS tag for preparing a lectin plate of the present invention is a peptide containing "RIIIRRIRR (SEQ ID NO: 2)", or "RSSSRRSRR (SEQ ID NO: 9)", and the former is also referred to as a PSI tag, and the latter is also referred to as a PSS tag.

Further, since the PS tag has compatibility with every kind of lectin, it is preferred to select and use appropriately a PS tag having favorable compatibility in response to the kind of the lectin to be immobilized.

(1-3) With Respect to PMMA/PC Tag

The PMMA/PC tag that can be used in the present invention has a high affinity for a solid phase in a case of the solid phase whose surface is mainly a polycarbonate or polymethyl methacrylate resin. A polycarbonate resin is widely used as an engineering plastic, and a polymethyl methacrylate resin is used as a substrate for protein chips or the like (Patent Document 4).

Specifically, for example, among the PMMA tags, a peptide tag containing "SEQ ID NO: 21 (DVEGIGDVD-LVNYFEVGATYYFNK)" that is called a PMOMP25 peptide in Patent Document 4, and the like can be mentioned, but the tag is not limited to the peptide tag, and any of the peptides disclosed in Patent Document 4 can also be used.

(1-4) With Respect to SiN Tag

The PC tag that can be used in the present invention has a high affinity for a solid phase in a case of the solid phase whose surface is silicon nitride ($Si_3N_4$). Silicon nitride is widely used as a semiconductor material (Patent Document 5).

Specifically, among the SiN tags, a peptide tag containing "SEQ ID NO: 22 (GGRHTPFFKGYRPQFYFRTTDV-TGTIELPE)" that is called a V821 peptide in Patent Document 5, and the like can be mentioned, but the tag is not limited to the peptide tag, and any of the peptides disclosed in Patent Document 5 can also be used.

(1-5) With Respect to PDMS Tag

The PDMS tag that can be used in the present invention has a high affinity for a solid phase in a case of the solid phase whose surface is polydimethylsiloxane being one kind of silicone rubber. Polydimethylsiloxane is known as one of substrates for microchips such as microfluidic flow paths (Patent Document 6).

Specifically, among the PDMS tags, a peptide tag containing "SEQ ID NO: 23 (MVMPGDNIKMVVTLIHPI-AMDDGLRFAIRE)" that is called an ELN-V81 peptide in Patent Document 6, and the like can be mentioned, but the tag is not limited to the peptide tag, and any of the peptides disclosed in Patent Document 6 can also be used.

2. Kind of Lectin to be Immobilized of the Present Invention

The lectin of the present invention may be any lectin capable of recognizing a specific target sugar chain, but in order to bind the lectin to a tag for immobilization of the present invention, such as a PS tag, it is preferred to obtain a recombinant body by connecting a gene encoding a PS tag or the like to a lectin gene, and therefore, it is preferred to use a lectin of which the full-length amino acid sequence or the amino acid sequence containing at least a sugar chain recognition site is known.

For example, rACG, rPSL1a, rLSLN, rDiscoidin I, rDiscoidin II, rCGL2, rSRL, rF17AG, rGRFT, rOrysata, rCalsepa, rBC2LA, rAAL, rPAIIL, rRSIIL, rPPL, rCNL, rPAIL, rABA, rMOA, rPALa, rGal3CS, rMpL, rAAL2, rBambL, and rPVL lectins can be mentioned, however, the lectin of the present invention is not limited to these lectins.

In addition, characteristics such as the origin and sugar chain specificity of these lectins are described in "Lectin Frontier DataBase (LfDB) (acgg.asia/lfdb2/)" or the like, and all of the lectins are commercially available as recombinant lectins from Wako Pure Chemical Industries, Ltd., or the like.

Further, the tag for immobilization of the present invention is preferably selected appropriately from the tags for immobilization of the present invention and used in response to the kind of the lectin to be immobilized at that time or in response to the kind of the surface of a solid phase for immobilization.

When a gene encoding a tag for immobilization of the present invention such as a PS tag is bound to the 5'-terminal or 3'-terminal of a lectin gene, in order to facilitate the detection and purification of a tagged lectin of a recombinant, the tagged lectin may be expressed as a fusion protein with a tag peptide such as a FLAG tag, a 3×FLAG tag, or a His tag (for example, 6×His tag), or another protein, at the 3'-terminal or 5'-terminal, which is each of the terminals on the opposite sides of the 5'-terminal and 3'-terminal.

In this regard, in a case where a lectin whose nucleic acid sequence is unknown, such as a naturally-derived lectin is used, the tag peptide for immobilization of the present invention can also be chemically bound directly to the target lectin.

In addition, the amino acid sequence of the lectin to be used in the present invention is not necessary to be the full length as long as it retains a recognition site of a specific target sugar chain, and may be a partial sequence having a recognition site of a target sugar chain.

Further, within the range not impairing the recognition ability for a specific target sugar chain, the deletion, substitution, addition, or insertion of amino acid residues is accepted as long as the amino acid residues to be deleted, substituted, added, or inserted is less than 10%, preferably less than 8%, more preferably less than 5%, furthermore preferably less than 3%, still furthermore preferably less than 2%, and particularly preferably less than 1% in the amino acid sequence. In terms of the number of amino acid residues, the deletion, substitution, addition, or insertion of amino acid residues is accepted as long as the amino acid residues to be deleted, substituted, added, or inserted is, for example, 20 or less residues, for example, 10 or less residues, for example, 5 or less residues, for example, 3 or less residues, for example, 2 or less residues, or for example, 1 residue. The position of the deletion, substitution, addition, or insertion at that time is preferably only the C-terminal or N-terminal of the amino acid sequence of the lectin.

In addition, also for the amino acid sequence of a lectin-peptide fusion to be used in the present invention, within the range not impairing the recognition ability for a specific target sugar chain and the adsorption ability specific for a solid phase (base material), the deletion, substitution, addition, or insertion of amino acid residues is accepted as long as the amino acid residues to be deleted, substituted, added, or inserted is less than 10%, preferably less than 8%, more preferably less than 5%, furthermore preferably less than 3%, still furthermore preferably less than 2%, and particularly preferably less than 1% in the amino acid sequence. In terms of the number of amino acid residues, the deletion, substitution, addition, or insertion of amino acid residues is accepted as long as the amino acid residues to be deleted, substituted, added, or inserted is, for example, 20 or less residues, for example, 10 or less residues, for example, 5 or less residues, for example, 3 or less residues, for example, 2 or less residues, or for example, 1 residue. The position of the deletion, substitution, addition, or insertion at that time is preferably only the C-terminal or N-terminal of the amino acid sequence of the lectin or peptide of the fusion.

3. Production of Tagged Lectin for Immobilization of the Present Invention (3-1) Vector for Producing Tagged Lectin for Immobilization of the Present Invention A nucleic acid sequence encoding a tag for immobilization of the present invention, such as a PS tag is connected to the 5'-terminal or 3'-terminal of the nucleic acid sequence encoding an amino acid sequence of the lectin having a binding ability for a target sugar chain, and preferably, a cassette in which a nucleic acid sequence encoding a FLAG tag has been connected to each of the terminals on the opposite sides of the 5'-terminal and 3'-terminal is incorporated into an appropriate vector for expression in accordance with a conventional method to obtain a recombinant vector for expression. In this regard, the amino acid sequence of the lectin having a binding ability for a target sugar chain does not have to be the full length, but has only to contain at least a binding site for the target sugar chain.

The expression vector is not particularly limited as long as it has a function to express and produce a tagged lectin for immobilization of the present invention as a fusion protein in various kinds of host cells. A commercially-available plasmid vector, phage vector, or virus vector can be used.

As the host cell, E. coli, Bacillus subtilis, Actinomyces, yeast, a filamentous fungus, a plant cell, an insect cell, an animal cell, or the like can be used, and E. coli is preferably used.

(3-2) Production Method of Tagged Lectin for Immobilization of the Present Invention Transformation of a host cell with a recombinant vector for expression can be performed by using a conventionally known method, and in a case where a commercially available competent cell is used, the transformation has only to be performed in accordance with the product protocol.

Further, a lectin whose nucleic acid sequence is unknown, such as a naturally-derived lectin, and a tag peptide for immobilization synthesized in advance by chemical synthesis or by gene recombination can be obtained as a fusion protein by using a coupling reaction of an normal protein with a peptide (for example, amine coupling using a NHS group, or diol coupling using a SH group, or a maleimide group), but the method is not limited to this method. A fusion method other than covalent bonding, such as streptavidin-biotin reaction can be used.

4. Base Material (Solid Phase) for Immobilizing Lectin of the Present Invention (2-1) Substrate of Immobilized Lectin As the base material (solid phase) for immobilizing a lectin-peptide fusion of the present invention, a plate (for example, a microwell plate), a microarray substrate (for example, slide glass for microarray), a tube, beads (for example, plastic beads, or magnetic beads), a carrier for chromatography (for example, Sepharose (trademark)), a membrane (for example, a nitrocellulose membrane, a PVDF membrane, a polystyrene nonwoven fabric), a gel (for example, polyacrylamide gel), and the like can be mentioned. Among them, a plate, beads, and a membrane are preferably used, and a plate is most preferably used from the viewpoint of the ease of handling.

Hereinafter, a case of a "lectin-peptide fusion binding plate" (also referred to as "tagged lectin plate") mainly using a plate will be described, but the solid phase of the present invention is not limited only to a plate.

In a case of using a PS tag, as to the quality of a plate, it is preferred that the plate has a hydrophilic resin surface, and a plate obtained by altering a surface of a plastic resin such as a polystyrene resin, a polycarbonate resin, a polypropylene resin, a polyethylene resin, a polydimethylsiloxane (PDMS) resin, or a polymethyl methacrylate (PMMA) resin to be hydrophilically treated can be used. In particular, it is preferred to use hydrophilic polystyrene, or polycarbonate for the plate.

Many of these hydrophilic resin plates are commercially available, but by performing UV+$O_3$ treatment or plasma oxidation treatment on a surface of a hydrophobic resin, the hydrophobic resin can be made hydrophilic.

(2-2) Production Method of Lectin-Peptide Fusion Binding Plate

In a case where a tagged lectin for immobilization of the present invention such as a PS-tagged lectin is produced from a transformed cell, a culture medium as it is, a cell disrupted liquid, or a soluble fraction obtained by centrifuging a cell disrupted liquid may be used as it is or after being appropriately diluted, however, it is preferred to use a solution in which fusion proteins purified by an ordinary protein purification method have been dissolved in an aqueous solvent. In a case of a chemically-synthesized fusion protein, a solution in which fusion proteins have been dissolved in an aqueous solvent is also used.

Conditions of a solution or suspension containing the tagged lectin for immobilization of the present invention are adjusted to optimized conditions in accordance with the methods described in Patent Documents 3 to 6, in response to the kind of the tag and the plate, and the solution or suspension under the adjusted optimized conditions is brought into contact with a surface of a base material (solid phase) such as a plate for immobilization.

(2-3) pH Condition and Salt Concentration Condition when Immobilizing Tagged Lectin When immobilizing a tagged lectin of the present invention, the immobilization is usually performed in the range of pH 6.0 to 8.0, however, in a case where a PS-tagged lectin is immobilized on a surface of a hydrophilic resin such as a hydrophilic polystyrene resin, the immobilization is performed in the range of preferably pH 6.5 to 7.5, and more preferably pH 7.0 to 7.5. In particular, in a case of using a PSI tag as the PS tag, it is preferred to use the PSI tag in the range of preferably pH 6.5 to 7.5, and particularly preferably around pH 7.0, for example, pH 6.8 to 7.2. In a case of using a PSS tag as the PS tag, it is preferred to use the PSS tag in the range of preferably pH 6.5 to 7.5, and particularly preferably around pH 7.5, for example, pH 7.3 to 7.7.

Further, the preferred salt concentration for immobilization is 0.05 to 0.30 M in terms of NaCl concentration, and more preferably 0.10 to 0.20 M, and the most preferred concentration is around 0.15 M, for example, 0.13 to 0.17 M in terms of NaCl concentration.

3. Measurement Method of the Present Invention and Kit for the Same (3-1) Sample to be Measured in the Present Invention By using a lectin-peptide fusion immobilized base material (lectin plate, or the like) of the present invention, the antigen containing a target sugar chain in a sample can be detected and/or measured (hereinafter, collectively referred to as "measured").

The sample to be measured of the present invention is a sample in which a sugar chain to be targeted, a glycoconjugate containing a target sugar chain, or a cell, extracellular vesicle, or virus having the target glycoconjugate (that is, "target sugar chain-containing antigen") may be present.

As the sugar chain or glycoconjugate to be targeted, in addition to various cell-specific sugar chains such as undifferentiated cell markers on a surface of a cultured cell or the like, a glycoconjugate such as a glycoprotein or a glycolipid, or a sugar chain or glycoconjugate in a culture supernatant, a disease-specific sugar chain or glycoconjugate observed in a body fluid such as blood of a test subject or test animal or on a surface of an organ, a tissue, or a cell, and the like can be mentioned.

That is, the sample to be measured of the present invention is a sample that may contain these target sugar chains or target glycoconjugates, and is a suspension, cell lysate, or cell culture supernatant containing cultured cells or cells themselves derived from a living body, or a suspension, purified solution, diluent or the like containing a body fluid such as blood derived from a test subject or test animal.

(3-2) Measurement Method Using Lectin-Peptide Fusion Binding Base Material (Tagged Lectin-Immobilized Base Material) of the Present Invention The measurement method to which a tagged lectin-immobilized base material of the present invention can be applied is typically an immunological measurement method such as ELISA, however, further, the tagged lectin-immobilized base material can be similarly applied also to an immunoassay method, radioimmunoassay (RIA), fluorescence immunoassay (FIA method), or chemiluminescence immunoassay. In addition, multiple lectins are immobilized on the same base material and can be used as a lectin array.

Hereinafter, typical sandwich ELISA will be described, but is not limited thereto.

<Sandwich ELISA>

The tagged lectin-immobilized plate (hereinafter, also simply referred to as "lectin plate) of the present invention can be used as a solid phase for sandwich ELISA.

For example, a solid phase (plate) to which PS-tagged lectin is bound is washed multiple times, and after blocking, the blocked solid phase is further washed multiple times. A sample containing a target substance is reacted with the lectin on the solid phase, and then the resultant sample is washed multiple times, the overlaid antibody is reacted with the target substance, and the washing is performed multiple times. There are multiple times of washing processes also after the reaction with an enzyme-labeled antibody that reacts with the overlaid antibody. The enzyme-labeled antibody is reacted with a substrate, the absorbance is measured, the target substance in the sample is detected, or the concentration is measured.

In a case of a PS-tagged lectin binding plate of the present invention, the amount of lectin is hardly reduced even when such washing processes are performed.

The antibody to be overlaid is preferably an antibody having binding activity with a protein moiety of a glycoprotein containing a target sugar chain, and the antibody can also be directly labeled.

Examples of the labeling substance include a fluorescence substance (such as FITC, rhodamine, Cy3, or Cy5), a radioactive substance (such as $^{13}C$, or $^3H$), an enzyme (such as alkaline phosphatase, or peroxidase), glucose oxidase, and β-galactosidase. Further, the antibody is labeled with biotin, streptavidin is labeled with the above labeling substance, and the binding between the biotin and the streptavidin may be utilized.

In a case where an enzyme is used as the labeling substance, the detection is performed by using an appropriate substrate corresponding to the enzyme to be used. For example, in a case where peroxidase is used as the enzyme, o-phenylenediamine (OPD), tetramethylbenzidine (TMB), or the like is used as the substrate. As to the enzyme reaction stop solution and the substrate solution, conventionally known solutions can be appropriately selected and used in response to the selected enzyme. Further, the measurement of a labeled signal may be performed by using an appropriate measuring device in response to the used labeling substance.

(3-3) Measurement Conditions and Selection of Blocking Agent

When measurement is performed by using a lectin plate of the present invention, the lectin plate is preferably washed with a PBS buffer solution containing a surfactant (for example, 0.1% Tween20) before and after the reaction with a labeled antibody for detection. In particular, the lectin plate before the reaction is preferably subjected to a blocking treatment with a blocking agent (for example, PBS buffer agent containing 2% BSA and 0.1% Tween20). Further, it is also effective to use the blocking agent (for example, PBS buffer agent containing 2% BSA and 0.1% Tween20) as a diluent for the labeled antibodies for detection to be reacted.

As the blocking agent at that time, in place of the 2% BSA-containing blocking agent, even if a blocking agent "Prevelex™ LS1004 (manufactured by Nissan Chemical Industries, Ltd.)" containing a composition for forming a coating film described in WO 2014/196650 is used, or even if Blocking One (manufactured by NACALAI TESQUE, INC.), or Blockmaster CE210 or CE510 (manufactured by JSR Life Sciences Corporation) is used, an approximately the same or higher reduction effect of a lower limit of detection (LLOD) value is exerted.

(3-4) Measurement Kit

A solid phase (lectin plate) on which one or more kinds of PS-tagged lectins of the present invention are immobilized can be used for various kinds of measurement kits such as an ELISA kit for measuring a target sugar chain or a target glycoconjugate. Further, it is preferred to form the kit with the combination of one or more kinds of labeled antibodies for detection, a blocking agent, a buffer solution, a diluent, and the like. Instructions for use and the like can also be included in the kit. In this regard, as the blocking agent, a blocking agent "Prevelex™ LS1004 (manufactured by Nissan Chemical Industries, Ltd.)" containing a composition for forming a coating film described in WO 2014/196650, or the like is preferred. In addition, as the diluent for the labeled antibodies for detection, an antibody diluent containing a blocking agent, in particular, a blocking agent containing a composition for forming a coating film is more preferably combined in the kit.

4. Separation Method Using Tagged Lectin of the Present Invention (4-1) Separation and Harvest of Cells With the use of a tagged lectin of the present invention, by using a sugar chain present on a surface of a cell to be separated and harvested as a target, only cells are concentrated, separated and/or harvested (hereinafter, collectively referred to as "separated") from the sample containing the cells.

Specifically, a lectin specific to a target sugar chain is immobilized on a base material (solid phase) of a bead such as a magnetic bead, a particle, a plate, or the like via a tag for immobilizing lectin of the present invention, the immobilized lectin is brought into contact with a sample containing a cell having a target sugar chain on a surface of the cell, and then the base material is thoroughly washed, and a monosaccharide solution specific to the lectin is allowed to act on the base material to harvest the cell.

For example, only a stem cell can be isolated from a body fluid sample, for example, blood of a mammal such as a human, or a cell-containing sample derived from a tissue, by using a stem-cell sugar chain marker or an undifferentiated-cell sugar chain marker as a target. As the target, by using a cancer-cell sugar chain marker, a sugar chain marker expressing specifically for a specific disease, or the like, a cancer cell and a lesion cell can also be isolated.

At that time, since the surface of a cell itself is negatively charged, it is preferred to use a PMMA tag (for example, SEQ ID NO: 21) as the tag for immobilization of the present invention.

(4-2) Separation (Concentration, Separation, Purification, and Harvest) of Glycoconjugate Such as Glycoprotein Separation (concentration or isolation) can be performed in a state of holding the binding to a lectin by a technique similar to that for measuring a glycoconjugate such as a glycoprotein. The harvest of glycoconjugates from lectin can be easily performed by allowing each lectin-specific monosaccharide solution to act on a sample.

(4-3) Separation Kit

A solid phase, for example, a bead such as a magnetic bead, a column, a plate, or the like on which one or more kinds of lectins with PS tags (preferably PMMA tags) of the present invention are immobilized can be used for a kit for concentrating, separating, and purifying a target sugar chain, or a target sugar chain-containing material (such as a target glycoconjugate, or a cell, an extracellular vesicle, a virus, or the like having a target glycoconjugate). Further, it is preferred to form the kit with the combination of one or more kinds of other lectins or antibodies recognizing a target sugar chain or a target glycoconjugate, a blocking agent, a buffer solution, a diluent, and the like. Instructions for use and the like can also be included in the kit.

In this regard, in a case of a combination with an antibody capable of recognizing a target glycoconjugate, it is preferred to combine the antibody with an antibody diluent containing a blocking agent, in particular, a blocking agent containing a composition for forming a coating film.

Further, as the separation kit of the present invention, an instruments, a device and the like including a separation column, a separation filter and the like can be included in the kit.

EXAMPLES

Hereinafter, the present invention will be specifically described with reference to Examples, however, the present invention is not limited to only the following Examples.

Other terms and concepts in the present invention are on the basis of the meanings of terms conventionally used in the field, and various techniques used to perform the present invention can be easily and reliably performed by those skilled in the art on the basis of known literature and the like particularly except for techniques whose sources have been clearly indicated. Further, the various analyses and the like were conducted according to the methods described in instruction manuals, catalogs, and the like for the analytical instrument, the reagent, and the kit, which were used.

Note that the contents of the technical literature, patent publications, and patent applications cited in the present specification are referred to as the contents of the present invention.

(Example 1) Synthesis of PSS-Tagged rBC2LCN and PSI-Tagged rBC2LCN Lectins

In the present Example, a rBC2LCN lectin was used as the lectin, a PSS tag (SEQ ID NO: 9) was selected together with a typical PSI tag (SEQ ID NO: 2) as the PS tag, and four kinds of constructs in each of which the tag had been bound on the N-terminal side or the C-terminal side of a rBC2LCN lectin were synthesized.

Specifically, four kinds of constructs (FIG. 1) in each of which a gene encoding any one of a PSI tag (SEQ ID NO: 2) or a PSS tag (SEQ ID NO: 9) was bound on the 5'-terminal side or 3'-terminal side of a gene encoding BC2LCN (SEQ ID NO: 24; GenBank/NCBI-GI registered number: YP_002232818 (Genome ID: 206562055)) and a FLAG tag was bound to the terminal on the opposite side of the 5'-terminal or 3'-terminal were synthesized, and each of the constructs was inserted into a pET27b vector.

Subsequently, the obtained vector was introduced to an *E. coli* (BL21-CodonPlus) host, and four kinds of BC2LCN lectins each with a corresponding PS tag were expressed.

Further, after disrupting cells, when the purification was performed with fucose agarose, in a case where a tag was added to the C-terminal side, 52 mg/L of PSI-tagged rBC2LCN, and 76 mg/L of PSS-tagged rBC2LCN were able to be purified (FIG. 2). On the other hand, in a case where a tag was added to the N-terminal side, 4 mg/L of PSI-tagged rBC2LCN, and 1 mg/L of PSS-tagged rBC2LCN were only able to be purified (FIG. 3).

From these results, it was found that at least as to the BC2LCN lectin, the yield of PS-tagged lectin was higher when the PS tag was added to the C-terminal side even in any case of the PSI and PSS tags. In addition, the yield of the PSS-tagged lectin was higher than that of the PSI-tagged lectin.

(Example 2) Yield Comparison of Recombinant PS-Tagged Lectin

As the lectin, a rACG lectin, a rPSL1a lectin, a rLSLN lectin, a rDiscoidin I lectin, a rDiscoidin II lectin, a rCGL2 lectin, a rSRL lectin, a rF17AG lectin, a rGRFT lectin, a rOrysata lectin, a rCalsepa lectin, a rBC2LA lectin, a rAAL lectin, a rPAIIL lectin, a rRSIIL lectin, a rPPL lectin, a rCNL lectin, a rPAIL lectin, a rABA lectin, a rMOA lectin, a rPALa lectin, a rGal3CS lectin, a rMpL lectin, a rAAL2 lectin, a rBambL lectin, or a rPVL lectin was selected, each gene of tags was bound to the lectin so that a PSI tag or PSS tag was bound to the C-terminal side of the lectin and a FLAG tag was bound to the terminal on the opposite side of the C-terminal side, and in a similar manner as in Example 1, purification was performed with fucose agarose after the expression in *E. coli*, and the yield of each of the PS-tagged lectins was measured.

As a result, it was found that the yield of the PSS-tagged lectin tended to be higher than that of the PSI-tagged lectin for almost all the lectins. Only in a case of rBambL, the yield of the PSI-tagged rBambL was higher than that of the PSS-tagged rBambL (FIG. 4).

(Example 3) Adsorption Amount of PS-Tagged Lectin on Various Kinds of Plates (3-1) rBC2LCN Lectin Untagged, PSI-tagged, or PSS-tagged rBC2LCN lectin was suspended in PBS or PBS with 0.1% Tween 20 (PBST), and the lectin suspended in PBS or PBST was allowed to react with various kinds of plates at various concentrations at room temperature for one hour. At that time, as the plate, a polystyrene plate for ELISA, that is, Nunc (260860) (manufactured by Thermo Fisher Scientific K.K.), Polysorp (manufactured by Thermo Fisher Scientific K.K.), or Maxisorp (manufactured by Thermo Fisher Scientific K.K.); a carboplate (manufactured by Sumitomo Bakelite Co., Ltd.) in which a hydrazide group was included by surface processing of Carbo-BIND; or an AGC plate (made of glass for tissue culture, and manufactured by IWAKI CO., LTD.) in which carboxylic acid, carbonyl, a hydroxyl group, and the like were included by irradiating a surface of the plate with oxygen plasma was used. In this regard, the hydrophilicity is AGC, carbo>Maxisorp, Nunc (260860)>>Polysorp.

After that, washing was performed with PBST five times, and then the amount of the lectin adsorbed onto a surface of each of the plates was measured by using a protein quantification kit of micro BCA assay (ThemoFisher) (FIG. 5).

As a result, it can be understood that in PBS, almost all of the plates showed a high amount of adsorption of up to 0.5 µg/well in a case of the PS-tagged lectin in any plate, however, in a case of the PSS-tagged lectin, the amount of adsorption was low in the Polysorp plate having the lowest hydrophilicity. The carboplate and the AGC plate showed a high amount of adsorption even in the presence of Tween20 (PBST), however, almost no adsorption was observed in the other plates.

That is, a rBC2LCN lectin plate with high density, which included an AGC plate or carboplate of a PSS- or PSI-tagged rBC2LCN lectin, was able to be provided.

(3-2) rACG Lectin

For the untagged, PSI-tagged, or PSS-tagged rACG lectin, the amount of the lectin adsorbed onto a surface of each plate was also measured by applying a method similar to that in (3-1).

As a result, in the presence of Tween20 (PBST), the carboplate and the AGC plate had adsorptivity in a case of the PS-tagged lectin, however, lectin was hardly adsorbed on the polystyrene plate for normal ELISA (Maxisorp, Nunc, or Polysorp) (data not shown). FIG. 6 shows only the cases of the carboplate and the AGC plate. Hereinafter, similarly, the cases of (FIGS. 7 to 20) show only the cases of the carboplate and the AGC plate.

(3-3) rLSLN Lectin

For the untagged, PSI-tagged, or PSS-tagged rLSLN lectin, the amount of the lectin adsorbed onto a surface of each plate was also measured by applying a method similar to that in (3-1).

As a result, the rLSLN lectin also showed a tendency similar to that of the rACG lectin in (3-2) (FIG. 7).

(3-4) rDiscoidin II Lectin

For the untagged, PSI-tagged, or PSS-tagged rDiscoidin II lectin, the amount of the lectin adsorbed onto a surface of each plate was also measured by applying a method similar to that in (3-1).

As a result, the rDiscoidin II lectin also showed a tendency similar to that of the rACG lectin in (3-2) (FIG. 8).

(3-5) rCGL2 Lectin

For the untagged, PSI-tagged, or PSS-tagged rCGL2 lectin, the amount of the lectin adsorbed onto a surface of each plate was also measured by applying a method similar to that in (3-1).

As a result, it was shown that in a case of the rCGL2 lectin, not only in the presence of PBS but also in the presence of Tween20 (PBST), in a case of the carboplate and the AGC plate, the tendency of the higher amount of adsorption in a case of the PS-tagged lectin was similar, but even if in a case of the PS-untagged rCGL2 lectin, the higher the concentration was, the higher the adsorptivity was (FIG. 9).

(3-6) rF17AG Lectin

For the untagged, PSI-tagged, or PSS-tagged rF17AG lectin, the amount of the lectin adsorbed onto a surface of each plate was also measured by applying a method similar to that in (3-1).

As a result, also in a case of the rF17AG lectin, a tendency similar to that of the rCGL2 lectin in (3-5) was shown (FIG. 10).

(3-7) rGRFT Lectin

For the untagged, PSI-tagged, or PSS-tagged rGRFT lectin, the amount of the lectin adsorbed onto a surface of each plate was also measured by applying a method similar to that in (3-1).

As a result, in a case of the rF17AG lectin, a tendency similar to that of the rACG lectin in (3-2) was shown (FIG. 11).

(3-8) rOrysata Lectin

For the untagged, PSI-tagged, or PSS-tagged rOrysata lectin, the amount of the lectin adsorbed onto a surface of each plate was also measured by applying a method similar to that in (3-1).

As a result, in a case of the rOrysata lectin, in the presence of Tween20 (PBST), the adsorbability was only slightly observed if the concentration was high in a case of the PS-tagged lectin, and almost no adsorbability was observed in a case of the PS-untagged rOrysata lectin (FIG. 12).

(3-9) rCalsepa Lectin

For the untagged, PSI-tagged, or PSS-tagged rCalsepa lectin, the amount of the lectin adsorbed onto a surface of each plate was also measured by applying a method similar to that in (3-1).

As a result, in a case of the rCalsepa lectin, a tendency similar to that of the rACG lectin in (3-2) was shown (FIG. 13).

(3-10) rRSIIL Lectin

For the untagged, PSI-tagged, or PSS-tagged rRSIIL lectin, the amount of the lectin adsorbed onto a surface of each plate was also measured by applying a method similar to that in (3-1).

As a result, in a case of the rRSIIL lectin, the adsorptivity in the presence of Tween20 (PBST) was higher than that in presence of PBS in a case of the PSI-tagged rRSIIL lectin, but almost no adsorption was observed in the presence of PBST in a case of the PSS-tagged rRSIIL lectin on the contrary (FIG. 14).

(3-11) rCNL Lectin

For the untagged, PSI-tagged, or PSS-tagged rCNL lectin, the amount of the lectin adsorbed onto a surface of each plate was also measured by applying a method similar to that in (3-1).

As a result, in a case of the rCNL lectin, a tendency similar to that of the rACG lectin in (3-2) was shown (FIG. 15).

(3-12) rGal3C Lectin

For the untagged, PSI-tagged, or PSS-tagged rGal3C lectin, the amount of the lectin adsorbed onto a surface of each plate was also measured by applying a method similar to that in (3-1).

As a result, in a case of the rGal3C lectin, a tendency similar to that of the rACG lectin in (3-2) was shown (FIG. 16).

(3-13) rPSL1a Lectin

For the untagged, PSI-tagged, or PSS-tagged rPSL1a lectin, the amount of the lectin adsorbed onto a surface of each plate was also measured by applying a method similar to that in (3-1).

As a result, in a case of the rPSL1a lectin, in the presence of Tween20 (PBST), the adsorbability was only slightly observed if the concentration was high in any case regardless of whether the lectin was PS-tagged or not (FIG. 17).

(3-14) rPALa Lectin

For the untagged, PSI-tagged, or PSS-tagged rPALa lectin, the amount of the lectin adsorbed onto a surface of each plate was also measured by applying a method similar to that in (3-1).

As a result, in a case of the rPALa lectin, in the presence of Tween20 (PBST), the adsorbability was only slightly observed if the concentration was high in a case of the PS-tagged rPALa lectin, and almost no adsorbability was observed in a case of the Ps-untagged rPALa lectin (FIG. 18).

(3-15) rBC2LA Lectin

For the untagged, PSI-tagged, or PSS-tagged rBC2LA lectin, the amount of the lectin adsorbed onto a surface of each plate was also measured by applying a method similar to that in (3-1).

As a result, in a case of the rBC2LA Lectin, completely different from the case of (3-1), results similar to those in a case of the rPALa lectin of (3-14) were obtained (FIG. 19).

(3-16) rPA1L Lectin

For the untagged, PSI-tagged, or PSS-tagged rPA1L lectin, the amount of the lectin adsorbed onto a surface of each plate was also measured by applying a method similar to that in (3-1).

As a result, in a case of the rPA1L lectin, in the presence of Tween20 (PBST), the adsorptivity was shown in a case of the PS-tagged rPA1L lectin, but almost no adsorptivity was shown in a case of the PS-untagged rPA1L lectin. The adsorptivity in a case of the PSI-tagged rPA1L lectin was higher than that of each of the PS-tagged rPA1L lectins (FIG. 20).

(Example 4) Optimization Conditions for Immobilizing Lectin (4-1) Optimization Conditions for pH By using a PSS-tagged rBC2LCN lectin and a PSI-tagged rBC2LCN lectin, in an ELISA system for detecting an undifferentiated sugar chain marker in a culture supernatant, the pH of a buffer solution when the lectin was immobilized was optimized.

The PSS-tagged rBC2LCN lectin or the PSI-tagged rBC2LCN lectin was adjusted so as to have a concentration of 0.5 µg/mL in each of buffer solutions with various pH values containing 0.1% Tween20 and 0.15 M NaCl, and 50 µL of the resultant mixture was added to a carboplate for ELISA (manufactured by Sumitomo Bakelite Co., Ltd.), and was left to stand at room temperature for one hour. After five times of washing, 250 µL of PBS containing 2% BSA and 0.1% Tween20 was added to the plate, and the resultant mixture was left to stand at room temperature for one hour for blocking.

Next, after washing, 50 µL of culture supernatant of human iPS cell 201B7 strain was added to the plate, and the resultant mixture was left to stand at room temperature for one hour. After washing, peroxidase-labeled R10G antibodies was applied by 50 µL to the plate, and the resultant mixture was left to stand at room temperature for one hour. After washing, 50 µL of TMB (manufactured by Wako Pure Chemical Industries, Ltd.) was added to the plate, after 30 minutes of color development, the reaction was terminated by adding 50 µL of 1 N hydrochloric acid to each well, and measurement was performed with a plate reader at a main wavelength of 450 nm and a sub-wavelength of 620 nm.

As a result, it was found that the lower limit of detection (LLOD) in a case of the PSS-tagged lectin was low at pH 6.5 to 8, and in particular, the lowest value of the lower limit of detection (LLOD) was obtained at pH 7.5. On the other hand, in a case of the PSI-tagged lectin, the LLOD was low at pH 6.5 to 7.5, and the lowest value was obtained at pH 7. The LLOD value was the lowest at pH 7.5 (HEPES buffer) in a case of the PSS tagged lectin among both of the PSI- and PSS-tagged lectins, and LLOD=21 cells/mL was obtained (FIG. 21). That is, it can be said that the optimal pH value when immobilizing lectin is pH=6.5 to 7.5, and preferably pH=7.0 to 7.5. In this regard, the LLOD value was calculated from the average value (Ave) and standard deviation value (SD) of n=3 by using the calculation formula LLOD=Ave+3.3 SD (hereinafter, the same applies).

(4-2) Optimization Conditions for NaCl Concentration

Next, the NaCl concentration was optimized by using a PSS-tagged rBC2LCN lectin under the condition of pH 7.5.

The PSS-tagged rBC2LCN lectin was adjusted so as to be 0.5 µg/mL with a HEPES buffer containing 0.1% Tween20 and NaCl at each concentration, and each of the resultant mixtures was applied by 50 µL to a carboplate for ELISA (manufactured by Sumitomo Bakelite Co., Ltd.), and was left to stand at room temperature for one hour. After five times of washing, PBS containing 2% BSA and 0.1% Tween20 was added to the carboplate by 250 µL, and the resultant mixture was left to stand at room temperature for one hour.

Next, after washing, 50 µL of culture supernatant of human iPS cell 201B7 strain was added to the carboplate, and the resultant mixture was left to stand at room temperature for one hour. After washing, 50 µL of peroxidase-labeled R10G antibodies was added to the carboplate, and the resultant mixture was left to stand at room temperature for one hour. After washing, 50 µL of TMB (manufactured by Wako Pure Chemical Industries, Ltd.) was added to the carboplate, after 30 minutes of color development, the reaction was terminated by adding 50 µL of 1 N hydrochloric acid to each well, and measurement was performed with a plate reader at a main wavelength of 450 nm and a sub-wavelength of 620 nm.

As a result, it was found that in a suspension with a HEPES buffer at pH 7.5 of PSS-tagged rBC2LCN, the lowest value of the lower limit of detection LLOD=220 cells/mL was obtained in a case where the NaCl concentration was adjusted to 0.15 M (FIG. 22). That is, it can be said that the preferred salt concentration for immobilization is 0.10 to 0.20 M in terms of NaCl concentration, and in particular, it is preferred to adjust the concentration in the vicinity of 0.15 M.

(Example 5) Comparison of LLOD Value and Variation Degree Between PS Tagging Method and Biotinylation Method In the present Example, by using a PSS- or PSI-tagged lectin plate by a PS tagging method and an avidin plate to which biotinylated lectin was bound, the lower limit of detection (LLOD) and the degree of variation (CV) were compared with those of the undifferentiated sugar chain marker in a culture supernatant of human iPS cell 201B7 strain.

(5-1) Standard Curve

A PPS-tagged rBC2LCN lectin was immobilized on a carboplate for ELISA (manufactured by Sumitomo Bakelite Co., Ltd.) under the optimized pH conditions and NaCl concentration conditions determined in (Example 4) (this is called a PS tagging method). For the comparison, a biotinylated rBC2LCN was immobilized on an avidin plate (manufactured by Sumitomo Bakelite Co., Ltd.) (this method is called a biotinylation method. Tateno, et al., Regenerative therapy 2017, in press). By using each of the plates, a standard curve in an ELISA system for detecting an undifferentiated sugar chain marker in a culture supernatant of human iPS cell 201B7 strain was created (FIG. 23).

(5-2) Production of PS-Tagged Lectin Plate

A buffer solution (PBS containing a HEPES buffer agent containing 150 mM of NaCl and 0.1% Tween20) that had been adjusted so that the PSS- or PSI-tagged rBC2LCN lectin was contained at 0.05 µg/mL was applied to a carboplate for ELISA (manufactured by Sumitomo Bakelite Co., Ltd.) at 50 µL/well, and the resultant mixture was incubated at room temperature for one hour.

The resultant plate was washed with a buffer solution, a blocking solution (2% BSA/0.1% Tween20 PBS) was applied to the washed plate at 250 µL/well, the resultant mixture was left to stand at room temperature for one hour, and the obtained plate was washed with a buffer solution.

A test sample (iPS cell) was diluted with a culture medium (mTeSR1), the diluted test sample was applied to the washed plate at 50 µL/well, the resultant mixture was incubated at room temperature for one hour, and the resultant plate was washed with a buffer solution. Next, horseradish peroxidase (HRP)-labeled antibodies (R10G (NH2)) were adjusted with a buffer solution (2% BSA/0.1% Tween20 PBS), the resultant mixture was applied to the washed plate at 50 µl/well. The resultant plate was incubated at room temperature for one hour, the obtained plate was washed with a buffer solution, a TMB solution was applied to the washed plate at 50 µl/well, and the resultant plate was incubated at room temperature. The reaction was terminated by adding 1 N HCL at 50 µl/well, the obtained plate was scanned with a plate reader (at a main wavelength of 450 nm and a sub-wavelength of 620 nm), and the absorbance was measured.

The above operation was performed in triplicate and the same operation was repeated three times.

(5-3) Production of Avidin Plate of Biotinylated Lectin

Streptavidin at 0.5 or 1 µg/mL (in PBS) was applied to a plate at 50 µL/well, and the resultant mixture was incubated at room temperature for one hour. The resultant plate was washed with a buffer solution, a blocking solution (2% BSA/0.1% Tween20 PBS) was applied to the washed plate at 250 µL/well, the resultant mixture was left to stand at room temperature for one hour, and the obtained plate was washed with a buffer solution.

The biotinylated rBC2LCN was diluted with PBS so as to be 0.3 µg/mL, the diluted biotinylated rBC2LCN was applied to the washed plate at 50 µL/well, the resultant mixture was incubated at room temperature for one hour, and then the resultant plate was washed with a buffer solution.

A test sample (iPS cell) was diluted with a culture medium (mTeSR1), the diluted test sample was applied to the washed plate at 50 µL/well, the resultant mixture was incubated at room temperature for one hour, and the resultant plate was washed with a buffer solution five times. Next, 1 µg/mL of HRP-labeled antibodies (R10G (NH2)) was adjusted with a buffer solution (2% BSA/0.1% Tween20 PBS), the resultant mixture was applied to the washed plate at 50 µl/well. The resultant plate was incubated at room temperature for one hour, the obtained plate was washed with a buffer solution, a TMB solution was applied to the washed plate at 50 µl/well, and the resultant mixture was incubated at room temperature for 30 minutes. The reaction was terminated by adding 1 N HCL at 50 µl/well, the obtained plate was scanned with a plate reader (at a main wavelength of 450 nm and a sub-wavelength of 620 nm), and the absorbance was measured.

The above operation was performed in triplicate and the same operation was repeated three times.

(5-4) Comparison of Degree of Variation

In each of the cases where a PSS- or PSI-tagged lectin plate and a biotinylated lectin-avidin plate were used, a coefficient of variation (CV) representing the degree of variation of each of the signals used in a calibration curve was calculated. The same experiment was performed three times, and the average value of CV was calculated (FIG. 24). As to the degree of variation, there was no significant difference between the PSI-tagged lectin plate and the avidin plate, however, the results showed that the coefficient of variation (CV) average value was the lowest and thus the degree of variation was the lowest in a case of the PSS-tagged lectin plate.

(5-5) Comparison of LLOD Value

In each of the cases where a PSS- or PSI-tagged lectin plate and a biotinylated lectin-avidin plate were used, comparison of the lower limit of detection (LLOD) of an undifferentiated sugar chain marker in a culture supernatant of human iPS cell 201B7 strain was performed.

In this regard, the LLOD was calculated by using the calculation formula of "LLOD=Ave+3.3 SD" from the average value (Ave) obtained as a result (cells/mL) of repeating the same experiment three times.

As a result, in any case of the PS-tagged lectin plates, the PS-tagged lectin plate showed a value lower than that in a case of using the avidin plate in the lower limit of detection (LLOD), and in particular, the lowest value was shown in a case of the PSI-tagged lectin plate (FIG. 25).

(Example 6) Reactivity Comparison of PS-Tagged rBC2LCN Lectin with iPS Cells

In a similar manner as in the method in (Example 1), rBC2LCN in which the C-terminal side was PSI tagged or PSS tagged was prepared, the PSI- or PSS-tagged rBC2LCN and the PS-untagged rBC2LCN were respectively suspended in PBS or PBST (0.25 µg/well), and each of the resultant mixtures was immobilized on a carboplate (manufactured by Sumitomo Bakelite Co., Ltd.) at room temperature for one hour. After washing the plate with PBST, 2% BSA/PBST was added to the washed plate at 250 µL/well, and the resultant mixture was blocked at room temperature for one hour.

Next, a hydrophobic fraction prepared from a human iPS cell 201B7 (obtained from Riken BioResource Research Center, Independent Administrative Agency) was biotinylated, and the biotinylated fraction was allowed to react at different concentrations at room temperature for one hour. To the resultant fraction, 10 ng/mL of peroxidase-labeled streptavidin was added at 50 µL/well, the reaction was performed at room temperature for one hour, and then a substrate was added to the resultant mixture to develop color. After the lapse of 30 minutes at room temperature, 1 N hydrochloric acid was added to the mixture at 50 µL/well to terminate the reaction, and then the measurement was performed at a main wavelength of 450 nm and a sub-wavelength of 620 nm (FIG. 26).

As a result, the PSS- or PSI-tagged rBC2LCN lectin showed significantly higher signals as compared with those of the PS-untagged rBC2LCN lectin, and in both of the PSS- and PSI-tagged rBC2LCN lectins, the reactivity of the PSS-tagged rBC2LCN lectin was higher than that of the PSI-tagged rBC2LCN lectin.

In particular, in a case of the PSS-tagged rBC2LCN lectin, even in the presence of Tween20 (PBST), stable reactivity with almost the same degree as that in the presence of PBS was shown (FIG. 27). This can be presumed that in the PSS-tagged rBC2LCN lectin, the high reactivity with a target sugar chain can be maintained even in the presence of contaminants derived from the test sample in the reaction system.

When a target sugar chain on a surface of a cell is directly detected by using a cell lysate, a technique in which a cell lysate or a hydrophobic fraction thereof is labeled with biotin and detected with HRP-labeled streptavidin is generally used. In that case, an avidin plate cannot be used as the lectin plate, and therefore, the usefulness of the PSS/PSI-tagged lectin plate is extremely high in that respect.

(Example 7) Detection Lower Limit of PS-Tagged rBC2LCN Lectin

A PS-untagged, and PSI- or PSS-tagged rBC2LCN, which had been used in (Example 6), were each suspended in PBS or PBST (0.25 µg/well), the resultant mixture was immobilized on a carboplate (manufactured by Sumitomo Bakelite Co., Ltd.) at room temperature for one hour, and then the mixture was allowed to react with a human iPS cell 201B7 at different concentrations, and the lower limit of detection (LLOD) was measured.

As a result, it was found that the PSS/PSI-tagged rBC2LCN showed the sensitivity 10 to 200 times higher than that of the untagged rBC2LCN. When comparing the case of the PSI tag with the case of the PSS tag, the PSS-tagged rBC2LCN showed higher sensitivity (FIG. 28).

From the results of (Example 6) and (Example 7), it is considered that in a case of the PS-tagged, in particular, the PSS-tagged rBC2LCN, the cluster effect inherent in lectin can be exerted by orienting the rBC2LCN with high density on a plate, and the binding ability for a target sugar chain is increased, and the sensitivity is dramatically increased.

(Example 8) Reactivity Comparison of Various Lectins with Undifferentiated Sugar Chain Marker Various kinds of PSS/PSI-tagged lectins, each of which had been suspended in PBS or PBST, were each immobilized on a carboplate (manufactured by Sumitomo Bakelite Co., Ltd.) at 100 µg/well at room temperature for one hour. After washing the plate with PBST, 2% BSA/PBST was added to the washed plate at 250 µL/well, and the resultant mixture was blocked at room temperature for one hour.

A hydrophobic fraction prepared from a human iPS cell 201B7 or a human skin fibroblast (obtained from ATCC) was biotinylated, and reaction of the biotinylated fraction was performed at different concentrations at room temperature for one hour. To the resultant fraction, 10 ng/mL of peroxidase-labeled streptavidin was added at 50 µL/well, the reaction was performed at room temperature for one hour, and then a substrate was added to the resultant mixture to develop color. After the lapse of 30 minutes at room temperature, 1 N hydrochloric acid was added to the mixture at 50 µL/well to terminate the reaction, and then the measurement was performed at a main wavelength of 450 nm and a sub-wavelength of 620 nm.

As a result, in a case of the rBC2LCN lectin, the PSS- or PSI-tagged rBC2LCN lectin showed significantly higher signals as compared with those of the PS-untagged rBC2LCN lectin.

On the other hand, all of other lectins hardly have difference in the reactivity between the cases of the human iPS cell and the human skin fibroblast, and the difference in reactivity due to the PS tagging is not much large. However, in cases of rGRFT, rPSL1a, and rLSLN, the reactivity was increased due to the PS tagging, and in a case of PSI-tagged rRSIIL, the reactivity was increased only in a case of the human iPS cell. Further, these tendencies were not greatly affected by the presence or absence of Tween20.

(Example 9) Search for Optimization Condition Minimizing LLOD Value and Degree of Data Variation of PS-Tagged Lectin-Immobilized Plate In the present experiment, with the combination of a human iPS cell and a carboplate for ELISA on which PS-tagged rBC2LCN lectin had been immobilized, which was used in (Example 6) and the like, the optimization of the washing solution and blocking solution in each process of the reaction so that the LLOD value of reaction intensity measurement and the degree of data variation were minimized was investigated, and the results were compared with those in the avidin plate on which biotinylated lectin had been immobilized by a conventional method.

(9-1) Experimental Method
<Condition 1>

A PS-tagged lectin (rBC2LCN) was adjusted to 0.5 µg/mL with a buffer solution (50 mM HEPES/150 mM NaCl 0.1% Tween20), and the resultant mixture was applied to each well of a carboplate for ELISA (S-BIO MS-8708F) by 50 µL. After the resultant mixture was left to stand at room temperature for one hour, the immobilized PS-tagged lectin was washed with (0.1% Tween20/PBS at 350 µL/well, hereinafter also simply referred to as "0.1% Tween20/PBS"), and the washing solution was removed.

A dilution series was prepared by adding a culture medium to iPS cells (201B7 sup) as a test sample, and was applied to each PS-tagged lectin-immobilized well by 50 µL, and after the resultant mixture was left to stand at room temperature for one hour, the resultant plate was washed five times with (0.1% Tween20/PBS), and the washing solution was removed.

Next, a labeled antibody solution for detection, in which peroxidase-labeled antibodies had been adjusted with PBS so as to be 2 µg/mL, was applied to each well by 50 µL, and the resultant mixture was left to stand at room temperature for one hour.

After washing the plate with (0.1% Tween20/PBS), a substrate was applied to each well by 50 µL. As a reaction stop solution, 1 N hydrochloric acid was applied by 50 µL to each well that had been left for 30 minutes. The absorbance was measured with a plate reader (at a main wavelength of 450 nm and a sub-wavelength of 620 nm). In this regard, as the control (control medium), only a culture medium that had not been used for cell culture was used for analysis, and the results of the analysis were used.
<Condition 2>

In a similar manner as in <Condition 1>, a PS-tagged lectin was immobilized in each well of a carboplate for ELISA (S-BIO MS-8708F), and was subjected to a process of washing with (0.1% Tween20/PBS) and washing solution removal, a process of reacting a dilution series of test cells (iPS cells: 201B7 sup) in each well, and a process of washing with (0.1% Tween20/PBS) and washing solution removal.

Next, as a labeled antibody solution for detection, a solution, in which peroxidase-labeled antibodies had been adjusted with 2% BSA/0.1% Tween20 PBS so as to be 2 µg/mL, was applied to each well by 50 µL, each well was sealed, and the resultant mixture was left to stand at room temperature for one hour.

In a similar manner as in <Condition 1>, a process of washing with (0.1% Tween20/PBS), a process of washing solution removal, a process of reaction with TMB, a process of reaction termination, and a process of absorbance measurement were performed.

<Conditions 3>

In a similar manner as in <Condition 1>, a PS-tagged lectin was immobilized in each well of a carboplate for ELISA (S-BIO MS-8708F), and was subjected to a process of washing with (0.1% Tween20/PBS) and washing solution removal.

Subsequently, PBS containing 2% BSA/0.1% Tween20 was applied to each well by 250 µL, and the resultant mixture was left to stand at room temperature for one hour, the washing with PBS at 350 µL/well was performed, and the washing solution was removed.

A dilution series of test cells (iPS cells: 201B7 sup) was applied to each well by 50 µL, and after the resultant mixture was left to stand at room temperature for one hour, washing was performed by using PBS as the washing solution at 350 µL/well, and the washing solution was removed.

Next, as a labeled antibody solution for detection, a solution, in which peroxidase-labeled antibodies had been adjusted with 2% BSA/0.1% Tween20 PBS so as to be 2 µg/mL, was applied to each well by 50 µL, and the resultant mixture was left to stand at room temperature for one hour.

Washing was performed by using PBS as the washing solution at 350 µL/well, and the washing solution was removed, and then in a similar manner as in <Condition 1>, a process of reaction with TMB, a process of reaction termination, and a process of absorbance measurement were performed.

<Condition 4>

An avidin plate (blocking-less type S-BIO BS-X7603) was washed twice with a washing solution (0.1% Tween20/PBS) at 350 µL/well, and biotinylated rBC2LCN that had been adjusted with a PBS buffer solution so as to be 0.3 µg/mL was applied to each well by 50 µl. After the resultant mixture was left to stand at room temperature for one hour, washing was performed five times by using 0.1% Tween20/PBS as the washing solution at 350 µL/well, and the washing solution was removed.

A dilution series of test cells (iPS cells: 201B7 sup) was applied to each well by 50 µL, and after the resultant mixture was left to stand at room temperature for one hour, washing was performed by using 0.1% Tween20/PBS as the washing solution at 350 µL/well, and the washing solution was removed.

Next, as a labeled antibody solution for detection, a solution, in which peroxidase-labeled antibodies had been adjusted with PBS so as to be 1 µg/mL, was applied to each well by 50 µL, and the resultant mixture was left to stand at room temperature for one hour.

Washing was performed by using 0.1% Tween20/PBS as the washing solution at 350 µL/well, the washing solution was removed, and then in a similar manner as in <Condition 1>, a process of reaction with TMB, a process of reaction termination, and a process of absorbance measurement were performed.

Each condition is summarized in the following table (Table 1).

TABLE 1

| Condition | 1 | 2 | 3 | 4 |
|---|---|---|---|---|
| Immobilized lectin Plate | PS-tagged rBC2LCN Carboplate (S-BIO MS-8708F) | PS-tagged rBC2LCN Carboplate (S-BIO MS-8708F) | PS-tagged rBC2LCN Carboplate (S-BIO MS-8708F) | Biotinylated rBC2LCN Avidin Plate (Blocking-less type) S-Bio Sumilon BS-X7603 |

TABLE 1-continued

| Condition | 1 | 2 | 3 | 4 |
|---|---|---|---|---|
| Blocking | — | — | 2% BSA/0.1% Tween20 PBS | — |
| Wash buffer | 0.1% Tween20/PBS | 0.1% Tween20/PBS | PBS | 0.1% Tween20/PBS |
| R-10G dilution solution | PBS | 2% BSA/0.1% Tween20 PBS | 2% BSA/0.1% Tween20 PBS | PBS |

(9-2) Optimization Condition

Each experiment was repeated three times, and the average values were taken, as a result of which in any case of the PSI tag and PSS tag, when comparing the <Condition 1> to <Condition 3> with one another, the highest absorbance was observed in a case where the experiment was performed under <Condition 1>. Further, in a case of the rBC2LCN lectin, the absorbance in a case of the PSS tag was higher than that in a case of the PSI tag (FIGS. 29 and 30).

In addition, with respect to the LLOD value, in a case of the PSI tag, the LLOD value was the lowest in a case of <Condition 2>, and in a case of the PSS tag, both of the LLOD values under <Condition 2> and <Condition 3> were low at the same level as each other. In any case, the LLOD value was lower than that in a case of <Condition 4> using an avidin plate, and in particular, in a case of <Condition 2>, in any case of the PSI tag and the PSS tag, the LLOD value was better than that with a significant difference in the results of the avidin plate (FIG. 31).

According to this, it can be considered that a method in which a blocking agent is added into a secondary antibody (R-10G) solution is effective.

(Example 10) Search for Blocking Agent for Minimizing LLOD Value of PS-Tagged Lectin-Immobilized Plate (10-1) Investigation of Various Kinds of Blocking Agents In the present experiment, in a similar manner as in (Example 9), by using the combination of a human iPS cell and a carboplate for ELISA on which a PS-tagged rBC2LCN lectin had been immobilized, a blocking agent that minimizes the LLOD value of the reaction intensity measurement was searched by using a protocol similar to that in Condition 3 under which the lowest LLOD was obtained in Example 9.

Specifically, in a similar manner as in <Condition 3>, after the PS-tagged rBC2LCN lectin was immobilized in each well of a carboplate for ELISA (S-BIO MS-8708F), peroxidase-labeled antibodies for detection were prepared so as to be 1 µg/mL by using a dilution obtained by diluting various kinds of blocking agents such as blocking agents shown in the following (Table 1) 10 times with 0.1% Tween20, and the absorbance was measured with a plate reader (at a main wavelength of 450 nm and a sub-wavelength of 620 nm) in accordance with the protocol of Condition 3 (FIG. 32).

N101 and N102 were not able to create the calibration curve, and therefore, the effects of the five kinds of blocking agents shown the following (Table 1), which were able to create the calibration curve, were examined in more detail as compared with BSA. In each case, the experiment was performed three times, and a graph was created by using the obtained average value and SD. As a result, it was found that the lowest LLOD was obtained with a coating agent-containing blocking agent "Prevelex™ LS1004 (manufactured by Nissan Chemical Industries, Ltd.)" among the cases of the rBC2LCN-PSS and a blocking agent (FIG. 33).

TABLE 2

| | Blocking reagents | | | | | |
|---|---|---|---|---|---|---|
| | Block Ace | Blocking One | Blockmaster CE210 | Blockmaster CE510 | Prevelex™ LS1004 | 2% BSA |
| | | | Company | | | |
| Cat# | DS Pharma Biomedical Co., Ltd. UKB80 | NACALAI TESQUE, INC. 03953-66 | JSR Life Sciences J-CE210RAN | JSR Life Sciences J-CE510RAN | NISSAN CHEMICAL Industries, Ltd. — | Wako Pure Chemical Industries Ltd. 016-15111 |
| rBC2L CN-PSI | 810.5 cells/mL | 316.7 cells/mL | 378.3 cells/mL | 586.8 cells/mL | 500.0 cells/mL | 234.8 cells/mL |
| rBC2L CN-PSS | 590.0 cells/mL | 255.5 cells/mL | 284.4 cells/mL | 244.1 cells/mL | 94.6 cells/mL | 218.6 cells/mL |

The invention claimed is:

1. A lectin-peptide fusion, comprising:
   a peptide capable of adsorbing to a base material surface; and
   a lectin capable of recognizing a target sugar chain, wherein
   the peptide is provided on an N-terminal side or a C-terminal side of the lectin,
   wherein the peptide is a PS peptide including a PSI tag having an amino acid sequence of SEQ ID NO: 2, or a PSS tag having an amino acid sequence of SEQ ID NO: 9.

2. The fusion according to claim 1, wherein
   the lectin is a lectin selected from the group consisting of a BC2LCN lectin, a rACG lectin, a rPSL1a lectin, a rLSLN lectin, a rDiscoidin I lectin, a rDiscoidin II lectin, a rCGL2 lectin, a rSRL lectin, a rF17AG lectin, a rGRFT lectin, a rOrysata lectin, a rCalsepa lectin, a rBC2LA lectin, a rAAL lectin, a rPAIIL lectin, a rRSIIL lectin, a rPPL lectin, a rCNL lectin, a rPAIL lectin, a rABA lectin, a rMOA lectin, a rPALa lectin, a rGal3CS lectin, a rMpL lectin, a rAAL2 lectin, a rBambL lectin, and a rPVL lectin.

3. The fusion according to claim 1, wherein the lectin is a BC2LCN lectin having the amino acid sequence of SEQ ID NO: 24.

4. A polynucleotide encoding a lectin-peptide fusion, wherein the lectin-peptide fusion comprises
   a peptide capable of adsorbing to a base material surface; and
   a lectin capable of recognizing a target sugar chain, wherein
   the peptide is provided on an N-terminal side or a C-terminal side of the lectin,
   wherein the peptide is a PS peptide including a PSI tag having an amino acid sequence of SEQ ID NO:2, or a PSS tag having an amino acid sequence of SEQ ID NO:9.

5. A vector capable of expressing a lectin-peptide fusion, comprising
   the polynucleotide of claim 4.

6. An immobilized lectin-peptide fusion, comprising:
   the lectin-peptide fusion according to claim 1; and
   a base material, wherein
   the peptide side in the lectin-peptide fusion is immobilized on the base material.

7. A base material, on which the lectin-peptide fusion according to claim 1 is immobilized.

8. A method for measuring or isolating a target sugar chain-containing antigen, comprising
   a process of bringing a sample containing a target sugar chain-containing antigen into contact with the base material according to claim 7.

9. The method according to claim 8, further comprising a process of overlaying an antibody capable of recognizing the target sugar chain-containing antigen.

10. The method according to claim 9, wherein
    in the process of overlaying an antibody capable of recognizing the target sugar chain-containing antigen, a blocking agent is contained in a diluent for a base material on which a lectin-peptide fusion is immobilized; and/or in a diluent for an antibody.

11. The method according to claim 9, wherein
    the target sugar chain-containing antigen is a sugar chain-containing antigen contained in a solution containing contaminants derived from a test sample.

12. A method for concentrating or isolating a cell having a target sugar chain or a glycoconjugate, comprising:
    a process of allowing a sample containing a cell having a target sugar chain on a surface of the cell or a glycoconjugate having a target sugar chain to adsorb to the base material according to claim 7; and
    a process of harvesting a target sugar chain-containing substance.

13. A kit or device for measuring or isolating a target sugar chain-containing antigen, comprising:
    the base material according to claim 7.

14. The kit or device according to claim 13, further comprising
    an antibody capable of recognizing the target sugar chain-containing antigen.

15. A method for producing a base material on which a lectin-peptide fusion is immobilized, comprising
    a process of bringing the lectin-peptide fusion according to claim 1 into contact with a base material.

16. The production method according to claim 15, wherein
    the process of bringing the lectin-peptide fusion into contact with a base material is performed in a buffer solution.

17. The production method according to claim 16, wherein
    the buffer solution has a pH of 6.5 to 7.5.

18. The production method according to claim 16, wherein
    the buffer solution has a salt concentration of 0.10 to 0.20 M.

* * * * *